ized Patent

(12) United States Patent
Boccoleri et al.

(10) Patent No.: US 10,653,498 B2
(45) Date of Patent: May 19, 2020

(54) FIBER OPTIC AND SLIP RING ROTARY JOINT FOR SUSPENSION ARM

(71) Applicant: Stryker Corporation, Kalamazoo, MI (US)

(72) Inventors: Gianni Ronald Boccoleri, Lantana, TX (US); Wojciech K. Timoszyk, Flower Mound, TX (US); David P. Chase, Southlake, TX (US)

(73) Assignee: Stryker Corporation, Kalamazoo, MI (US)

( * ) Notice: Subject to any disclaimer, the term of this patent is extended or adjusted under 35 U.S.C. 154(b) by 126 days.

(21) Appl. No.: 14/854,585

(22) Filed: Sep. 15, 2015

(65) Prior Publication Data

US 2016/0091117 A1 Mar. 31, 2016

Related U.S. Application Data

(60) Provisional application No. 62/056,878, filed on Sep. 29, 2014.

(51) Int. Cl.
| | |
|---|---|
| *G02B 6/36* | (2006.01) |
| *A61B 90/50* | (2016.01) |
| *F16M 13/02* | (2006.01) |
| *G02B 6/44* | (2006.01) |

(52) U.S. Cl.
CPC ............ *A61B 90/50* (2016.02); *G02B 6/3604* (2013.01); *F16M 13/02* (2013.01); *F16M 13/027* (2013.01); *F16M 2200/044* (2013.01); *F16M 2200/063* (2013.01); *F16M 2200/065* (2013.01); *G02B 6/4461* (2013.01)

(58) Field of Classification Search
CPC .................................................. G02B 6/3604

USPC ...................................................... 385/25, 26
See application file for complete search history.

(56) References Cited

U.S. PATENT DOCUMENTS

| | | | |
|---|---|---|---|
| 6,464,383 B1 | 10/2002 | Northington et al. | |
| 6,498,884 B1 * | 12/2002 | Colvin ............... | A61B 1/00167 |
| | | | 348/E5.029 |

(Continued)

FOREIGN PATENT DOCUMENTS

| | | | | |
|---|---|---|---|---|
| WO | WO 03/025453 A1 | | 3/2003 | |
| WO | WO 2014/075780 A1 * | | 5/2014 | ............. H01R 39/64 |

OTHER PUBLICATIONS

High Frequency Coaxial Cables; Subminiature & Miniature Coaxial Cables, p. 34, known before invention (1 page).
Tutorial: Wavelength Division Multiplexing and Directional Multiplexing from www.princetel.com, known before invention (4 pages).

(Continued)

*Primary Examiner* — Robert Tavlykaev
(74) *Attorney, Agent, or Firm* — Morrison & Foerster LLP

(57) ABSTRACT

A medical suspension arm assembly including a plurality of suspension arms, with each adjacent pair of the suspension arms being connected to each other by a joint and with at least one of the joints comprising an infinite rotation joint. The infinite rotation joint allows the suspension arms at the infinite rotation joint to have unlimited rotation relative to one another. Cabling including at least one fiber optic cable extends through each of the suspension arms and each joint. A wired medical unit is connected to an end of the plurality of suspension arms. High definition video, data and power can be transferred along each one of the suspension arms through the cabling and across each joint.

39 Claims, 12 Drawing Sheets

(56) References Cited

U.S. PATENT DOCUMENTS

| | | | |
|---|---|---|---|
| 7,474,852 B1* | 1/2009 | Jachetta | H04N 7/181 |
| | | | 398/33 |
| 7,792,400 B1 | 9/2010 | Zhang et al. | |
| 7,881,569 B2 | 2/2011 | Zhang et al. | |
| 8,355,607 B2 | 1/2013 | Zhang et al. | |
| 8,360,964 B2* | 1/2013 | Ertas | A61B 1/0005 |
| | | | 600/111 |
| 8,380,024 B1 | 2/2013 | Zhang et al. | |
| 8,417,075 B2 | 4/2013 | Violante et al. | |
| 8,997,362 B2* | 4/2015 | Briggs | G01B 11/005 |
| | | | 33/503 |
| 9,360,630 B2* | 6/2016 | Jenner | G02B 6/3604 |
| 2004/0251390 A1* | 12/2004 | Wachob | F16M 11/06 |
| | | | 248/323 |
| 2007/0053632 A1* | 3/2007 | Popp | G02B 6/3604 |
| | | | 385/26 |
| 2008/0225534 A1* | 9/2008 | Rus | F16G 13/16 |
| | | | 362/404 |
| 2009/0226131 A1* | 9/2009 | Zhang | G02B 6/3604 |
| | | | 385/26 |
| 2013/0044976 A1* | 2/2013 | Zhang | G02B 6/3604 |
| | | | 385/26 |
| 2014/0101953 A1* | 4/2014 | Briggs | G01B 11/005 |
| | | | 33/503 |
| 2014/0147077 A1* | 5/2014 | Doric | G02B 6/3604 |
| | | | 385/25 |

OTHER PUBLICATIONS

Tutorial: Electric Slip Rings from www.princetel.com, known before invention (7 pages).
How to mount fiber optic rotary joints from www.princetel.com, known before invention (5 pages).
FORJ: Miniature fiber rotary joints (MicroJx Series) from www.princetel.com, known before invention (1 page).
Model MJX Single-Channel FORJ and Model RFCX Single-Channel FORJ from www.princetel.com, known before invention (1 page).
Fiber Optic Rotary Joint Selection Guide, known before invention (1 page).
Tutorial: FORJ frequently asked questions from www.princetel.com, known before invention (5 pages).
Tutorial: Fiber optic rotary joint from www.princetel.com, known before invention (4 pages).
American Wire Gauge (AWG) Article, known before invention (3 pages).
Standards Article, known before invention (1 page).
RS-485 Article, pp. 1-6, known before invention (6 pages).
RS-232 Article, known before invention (1 page).
Serial Communication Article, pp. 1-4, known before invention (4 pages).
Compatibility Matters Brochure, Stryker Communications, 2007 (2 pages).
Twisted Pair Article, pp. 1-8, known before invention (8 pages).

\* cited by examiner

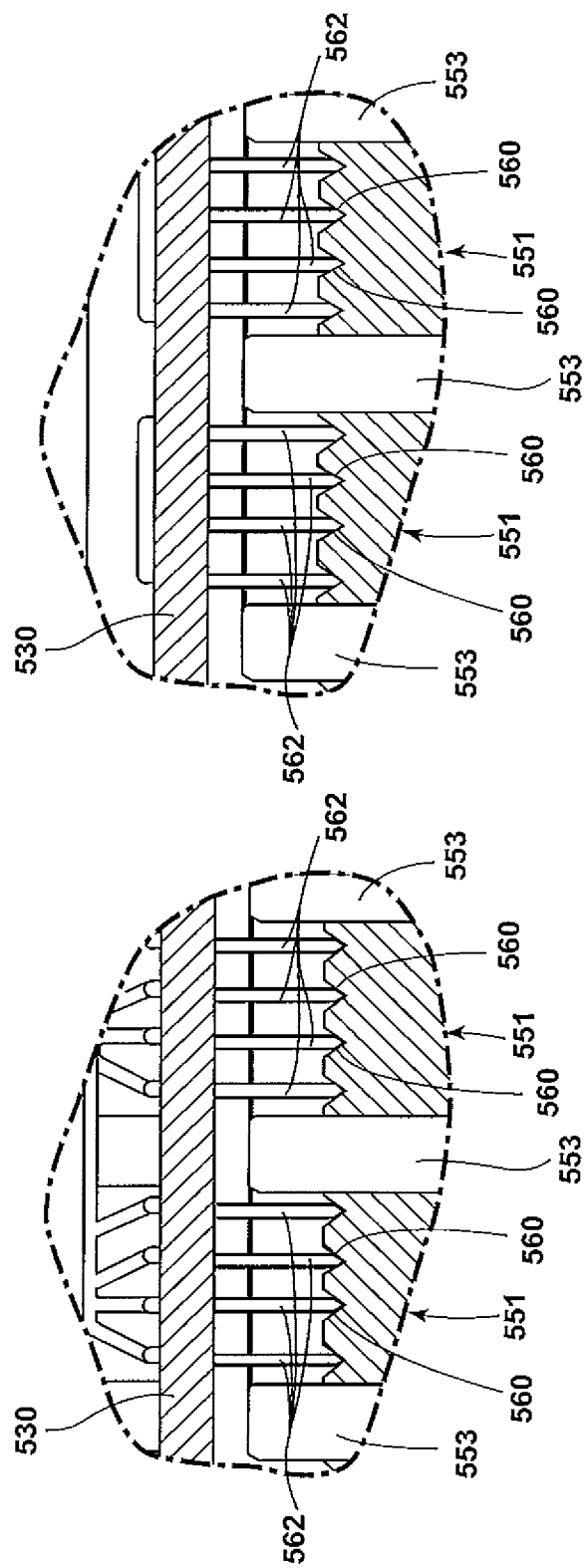

FIBER OPTIC AND SLIP RING ROTARY JOINT FOR SUSPENSION ARM

CROSS REFERENCE TO RELATED APPLICATION

This claims the benefit of U.S. Provisional Application Ser. No. 62/056,878, filed Sep. 29, 2014.

FIELD OF THE INVENTION

The present invention relates to a joint, and in particular to an infinite rotation fiber optic and slip ring joint that can be used in medical devices.

BACKGROUND OF THE INVENTION

Surgical monitors have been used in operating rooms to provide images to surgeons in the room. Likewise, other wired devices, such as surgical lights, speakers, joysticks, keyboards and cameras, have been used in operating rooms to provide surgical information to a surgeon or other person in the operating room (e.g., images from a camera or patient vital information). Such devices receive and/or provide signals and power to and/or from various supports mounted or provided in the operating room, thereby requiring wiring to extend through supports for such devices to the devices. Such wiring arrangements have necessitated that the rotation of joints of the supports be limited (e.g., using stops to limit rotation) to allow the wiring to extend fully through the supports without subjecting the wiring to excessive and damaging twisting of the wiring. Alternatively, if the rotation of the joints allowed for a larger range of rotation, such arrangements do not allow for a large data transfer rate of transmitted through the supports to the devices. Thus, there is a need for accommodating wiring in a way which will allow for a large data transfer rate while simultaneously allowing the supports to be fully and easily adjustable.

SUMMARY OF THE INVENTION

The present invention, according to one aspect, is directed to a medical suspension arm assembly including a plurality of suspension arms, with each adjacent pair of the suspension arms being connected to each other by a joint and with at least one of the joints comprising an infinite rotation joint. The infinite rotation joint allows the suspension arms at the infinite rotation joint to have unlimited rotation relative to one another. Cabling including at least one fiber optic cable extends through each of the suspension arms and each joint. A wired medical unit is connected to an end of the plurality of suspension arms. High definition video, data and power can be transferred along each one of the suspension arms through the cabling and across each joint.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

FIG. 10 is an enlarged cross-sectional view of a first area of the infinite rotation fiber optic and slip ring rotary joint according to the present invention taken from the circle X of FIG. 9A.

FIG. 11 is an enlarged cross-sectional view of a second area of the infinite rotation fiber optic and slip ring rotary joint according to the present invention taken from the circle XI of FIG. 9A.

Figure 1:
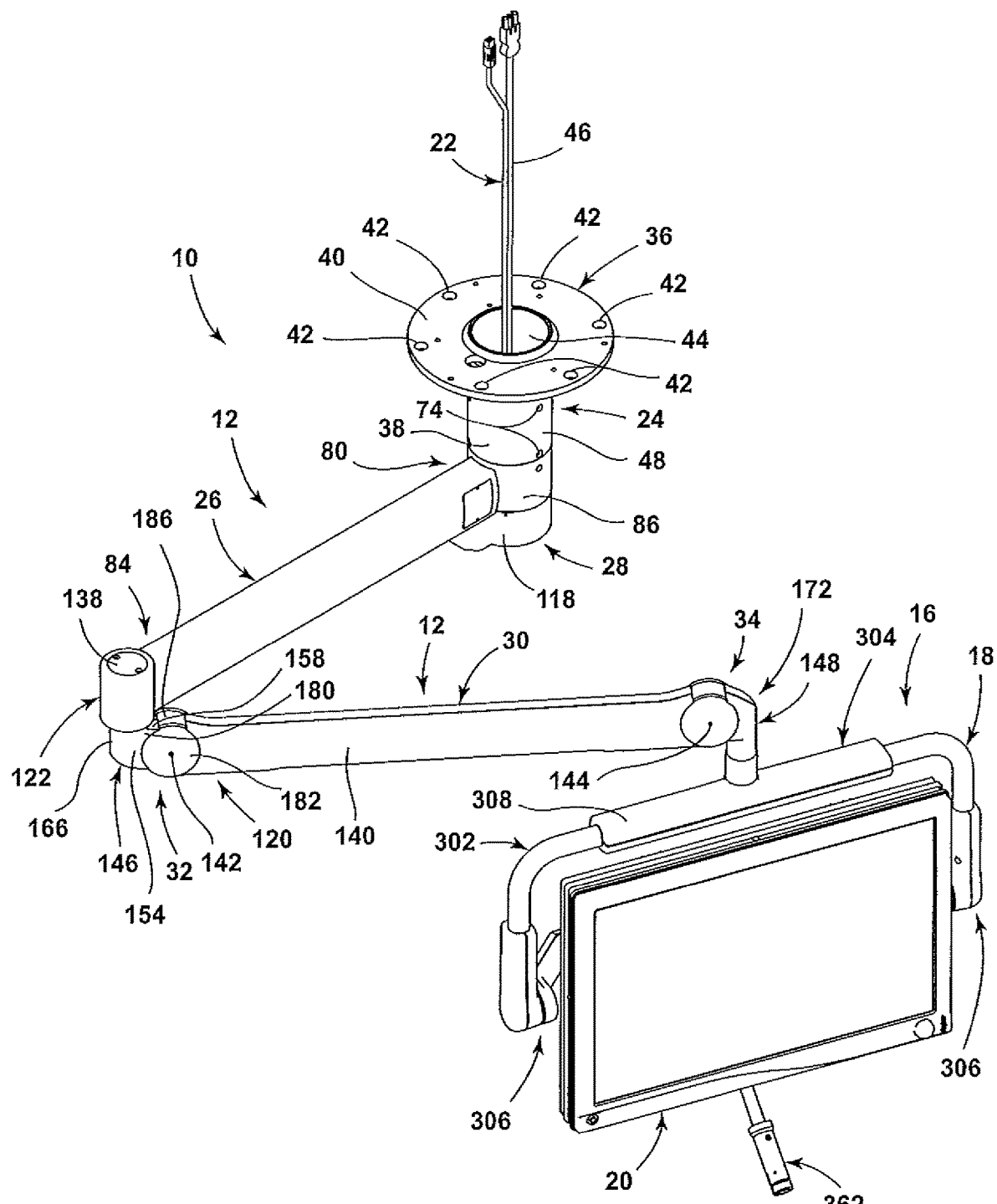
FIG. 1 illustrates a perspective view of a suspension arm assembly according to the present invention.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

The reference number 10 (FIGS. 1-4) generally designates a suspension arm assembly of the present invention. The suspension arm assembly 10 includes a ceiling attachment member 24, a wired medical unit 16 and a plurality of arms 12 between the ceiling attachment member 24 and the wired medical unit 16. The intersections between one of the arms 12 and the ceiling attachment member 24, each of the arms 12, and one of the arms 12 and the wired medical unit 16 allow for infinite rotation. Each intersection also includes an infinite rotation fiber optic and slip ring joint 14 (see FIGS. 3 and 4) therein. A cabling system 22 transmits data and power through the suspension arm assembly 10 to the wired medical unit 16 and the infinite rotation fiber optic and slip ring joints 14 allow for unlimited rotation of the arms 12 and the wired medical unit 16.

The illustrated suspension arm assembly 10 is configured to be positioned within a room (e.g., an operating room) and, in the illustrated embodiment, includes the wired medical unit 16, which is configured to provide information to the medical personnel in the room and/or to assist the medical personnel in the room perform various functions. In the illustrated example, the wired medical unit 16 includes a display support assembly 18 at a distal end of one of the arms 12 for supporting a display monitor 20 for providing surgical information to a surgeon or other person in the operating room (e.g., images from a camera (e.g., an in-light camera or an endoscopic camera) or patient vital information). It is contemplated that other items (e.g., surgical lights, dual displays, cameras, microphones, etc.) in addition to or instead of the display monitor 20 can be located at the end of the suspension arm assembly 10.

In the illustrated example, the suspension arm assembly 10 is connected to a ceiling and supports the wired medical unit 16 above a support surface, such as a floor. The suspension arm assembly 10 includes the ceiling attachment member 24, a first one of the arms 12 in the form of an extension arm 26 connected to the ceiling attachment member 24 at a first infinite rotation joint 28, a second one of the arms 12 in the form of a load counterbalancing spring arm 30 connected to the extension arm 26 by a second infinite rotation joint 32, and the display support assembly 18 connected to the load counterbalancing spring arm 30 with a third infinite rotation joint 34. While the suspension arm assembly 10 is illustrated as having two arms 12, it is contemplated that the suspension arm assembly 10 could have any number of arms 12 (including only one arm 12). Furthermore, while particular configurations of infinite rotation joints having the infinite rotation fiber optic and slip ring joint 14 are described below, it is contemplated that any configuration of infinite rotation joints having the infinite rotation fiber optic and slip ring joint 14 therein could be used. Moreover, while the suspension arm assembly 10 includes the ceiling attachment member 24 for connecting the suspension arm assembly 10 to a ceiling, it is contemplated that the ceiling attachment member 24 could be used to connect the suspension arm assembly 10 to any structure (fixed or movable) above a support surface, such as a floor.

The illustrated ceiling attachment member 24 accepts the cabling system 22 therein and supports the suspension arm assembly 10 from the ceiling of a room. The ceiling attachment member 24 includes a ceiling attachment flange 36 and a down tube 38. The ceiling attachment flange 36 can have any configuration for connecting to a ceiling support structure. In the illustrated embodiment, the ceiling attachment flange 36 is a flat circular disc 40 having a plurality of holes 42 therein configured to receive fasteners (not shown) for fixedly connecting the flat circular disc 40 to the ceiling support structure. The flat circular disc 40 includes a central opening 44 receiving a first section 46 of the cabling system 22 therethrough. The down tube 38 includes a down cylinder 48 being co-axial with the central opening 44 in the flat circular disc 40 of the ceiling attachment flange 36. The down tube 38 can have any axial length to adjust for various heights of ceilings in the room. The ceiling attachment member 24 further includes a central axis spindle 50 for connecting the down tube 38 to the extension arm 26.

Figure 5:
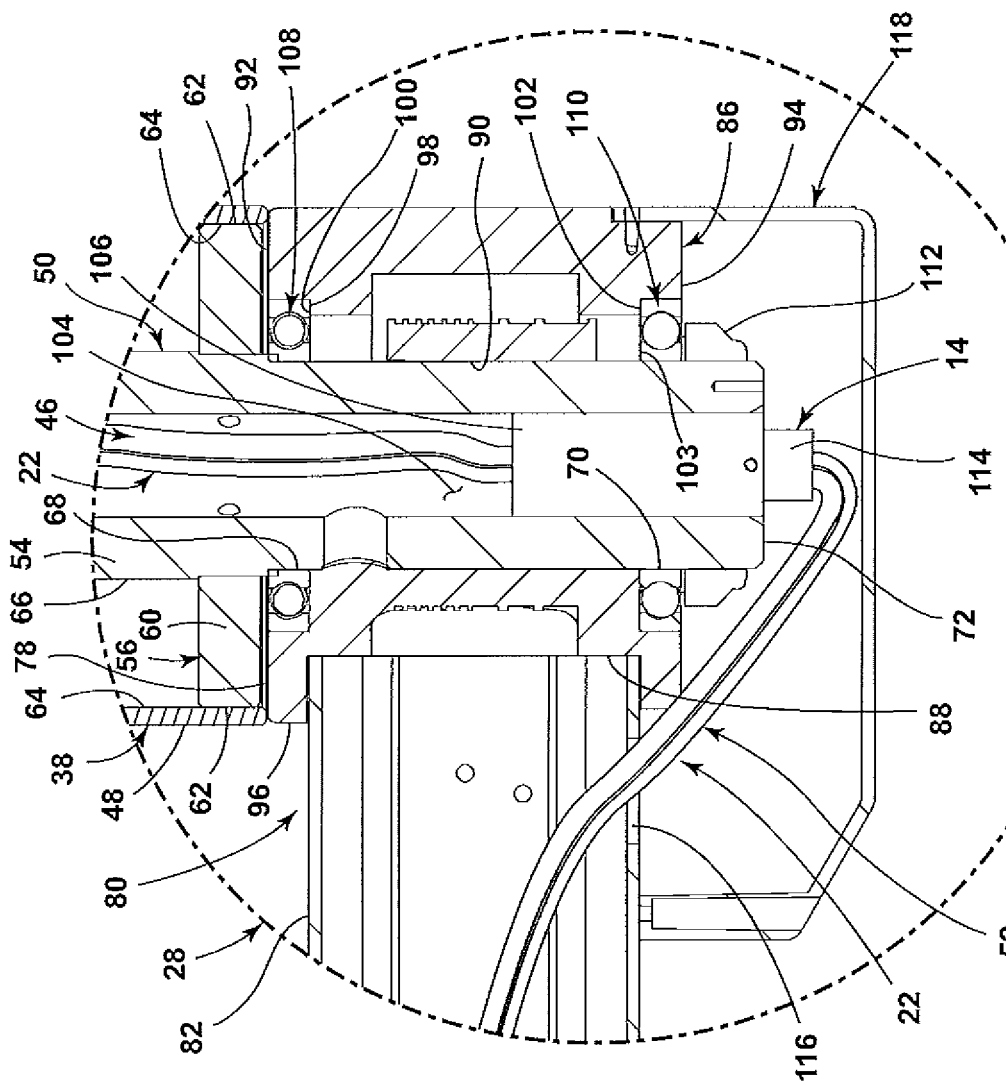
FIG. 5 is an enlarged cross-sectional view of a first infinite rotation joint of the suspension arm assembly according to the present invention taken from the circle V of FIG. 4.

In the illustrated example, the central axis spindle 50 allows for infinite rotation of the extension arm 26 about the ceiling attachment member 24 and houses one of the infinite rotation fiber optic and slip ring joints 14 therein connecting the first section 46 of the cabling system 22 to a second section 52 of the cabling system 22. The central axis spindle 50 includes an axis cylinder 54 having a pair of down tube mounting flanges 56 including an upper disc 58 and a lower disc 60. The upper disc 58 surrounds a top edge of the axis cylinder 54 and the lower disc 60 surrounds a central area of the axis cylinder 54. The upper disc 58 and the lower disc 60 have the same outer diameter corresponding to the inner diameter of the down cylinder 48 of the down tube 38 and have outer surfaces 62 which are aligned with one another such that the upper disc 58 and the lower disc 60 abut against an inner surface 64 of the down cylinder 48 of the down tube 38 (see FIG. 5). Fasteners (not shown) extend through aligned openings 74 in the down cylinder 48 and into openings 76 in the outer alignment surfaces 62 of the upper disc 58 and the lower disc 60 to fixedly connect the down cylinder 48 to the central axis spindle 50. As illustrated in FIG. 5, the lower disc 60 closes a bottom open end 78 of the down cylinder 48. An outer surface 66 of the axis cylinder 54 includes an upper bearing receiving area 68 located directly below the lower disc 60 and a lower bearing receiving area 70 located adjacent but spaced from a bottom edge 72 of the axis cylinder 54. The axis cylinder 54 also includes a bearing receiving surface below the lower bearing receiving area 70. The axis cylinder 54 receives the infinite rotation fiber optic and slip ring joint 14 therein and is received in a proximal end 80 of the extension arm 26.

The illustrated extension arm 26 is connected to the ceiling attachment member 24 at the first infinite rotation joint 28. The extension arm 26 includes a hollow tube 82 having the proximal end 80 connected to the ceiling attachment member 24 at the first infinite rotation joint 28 and a distal end 84 connected to the load counterbalancing spring arm 30 at the second infinite rotation joint 32. As illustrated in FIG. 5, the proximal end 80 of the extension arm 26 includes a spindle receiving block 86 receiving the central axis spindle 50 therein. The spindle receiving block 86 includes a side tube receiving counterbore 88 in a side face 96 thereof receiving an end of the hollow tube 82 therein for fixedly connecting the hollow tube 82 to the spindle receiving block 86. The spindle receiving block 86 further includes a central spindle receiving circular hole 90 that extends through the spindle receiving block 86 from a top surface 92 to a bottom surface 94 thereof. An upper bearing ring receiving counter bore 98 in the top surface 92 of the spindle receiving block 86 surrounds the central spindle receiving circular hole 90 to form a top step surface 100 located below the top surface 92. Likewise, a lower bearing ring receiving counter bore 102 in the bottom surface 94 of the spindle receiving block 86 surrounds the central spindle receiving circular hole 90 to form a bottom step surface 103 located above the bottom surface 94. In the illustrated example, the spindle receiving block 86 has a circular cross-section. However, it is contemplated that the spindle receiving block 86 could have any exterior shape.

In the illustrated example, the central axis spindle 50 is inserted into the spindle receiving block 86 of the extension arm 26 to allow the extension arm 26 to rotate about the axis cylinder 54 of the central axis spindle 50. During assembly of the suspension arm assembly 10, one of the infinite rotation fiber optic and slip ring joints 14 is connected to the first section 46 of the cabling system 22 (as discussed in more detail below) and inserted into an interior 104 of the axis cylinder 54 through the bottom edge 72 of the axis cylinder 54. A stator 106 of the infinite rotation fiber optic and slip ring joint 14 is then fixed to the axis cylinder 54 by fasteners (or any other connection method) such that the stator 106 of the infinite rotation fiber optic and slip ring joint 14 at the first infinite rotation joint 28 remains stationary relative to the room.

Figure 2:
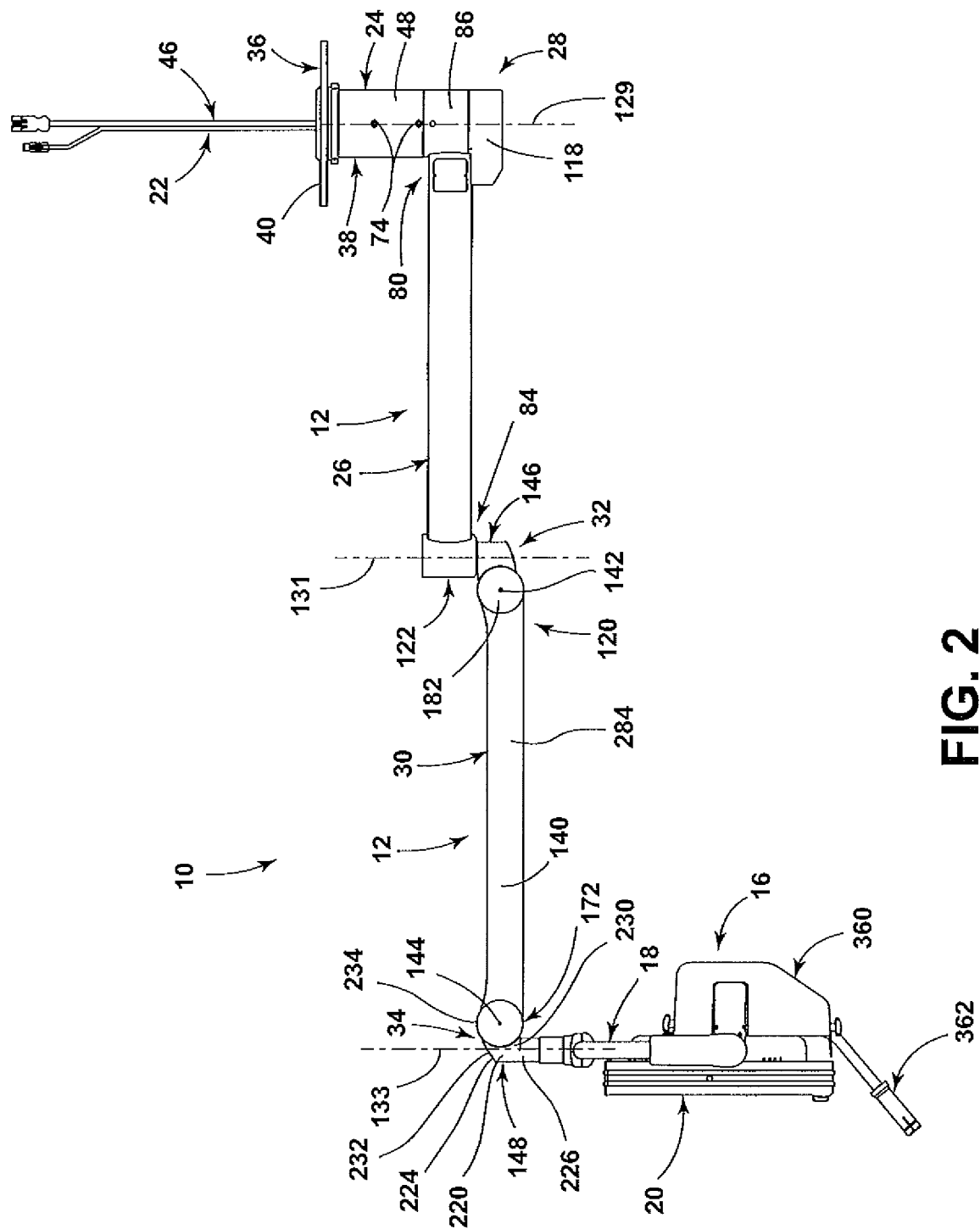
FIG. 2 is a side view of the suspension arm assembly according to the present invention.
Figure 3:
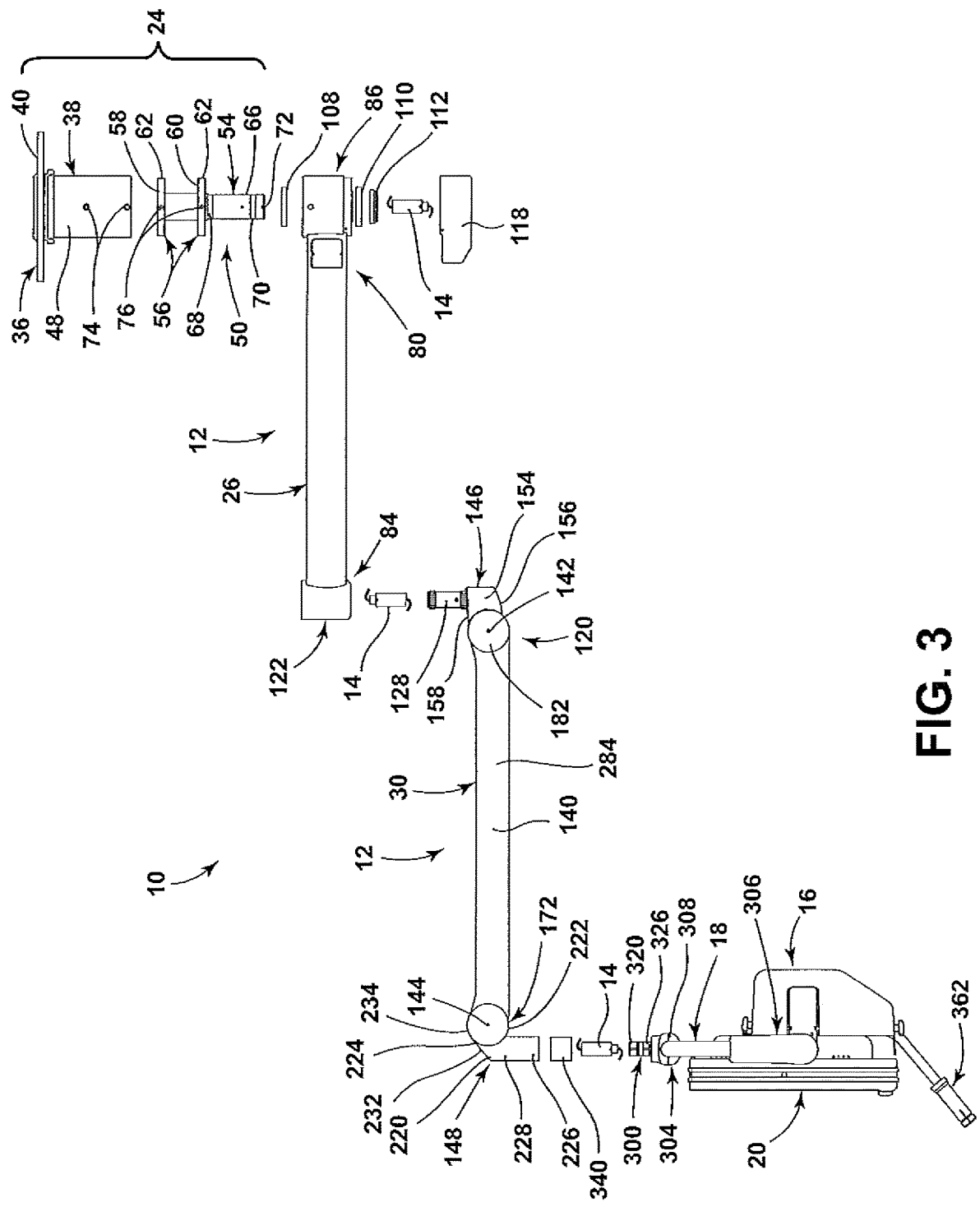
FIG. 3 is an exploded side view of the suspension arm assembly according to the present invention.

As illustrated in FIGS. 2 and 5, a first bearing ring 108 and a second bearing ring 110 allow the extension arm 26 to rotate relative to the ceiling attachment member 24 about a first vertical axis 129. The first bearing ring 108 surrounds the axis cylinder 54 at the upper bearing receiving area 68, with the lower disc 60 of the central axis spindle 50 resting on the first bearing ring 108. The first bearing ring 108 is located within the upper bearing ring receiving counter bore 98 in the top surface 92 of the spindle receiving block 86 and rides on the top step surface 100. The second bearing ring 110 surrounds the axis cylinder 54 at the lower bearing receiving area 70. The second bearing ring 110 is located within the lower bearing ring receiving counter bore 102 in the bottom surface 94 of the spindle receiving block 86, with the bottom step 103 resting on the second bearing ring 110. A disc shaped spanner nut 112 is connected to an end of the axis cylinder 54 (e.g., by being threaded onto the axis cylinder 54) to hold the second bearing ring 110 on the end of the axis cylinder 54. The disc shaped spanner nut 112 also compresses the second bearing ring 110 between the bottom step 103 of the lower bearing ring receiving counter bore 102 and the disc shaped spanner nut 112 such that the second bearing ring 110 rides on the disc shaped spanner nut 112. The disc shaped spanner nut 112 thereby ensures that the extension arm 26 is securely connected to the ceiling attachment member 24 to allow the extension arm 26 to rotate about the ceiling attachment member 24 in a stable manner.

In the illustrated example, a rotor 114 of the infinite rotation fiber optic and slip ring joint 14 is allowed to rotate relative to the stator 106 of the infinite rotation fiber optic and slip ring joint 14 and is connected to the second section 52 of the cabling system 22. Therefore, the rotor 114 of the infinite rotation fiber optic and slip ring joint 14 at the first infinite rotation joint 28 and the second section 52 of the cabling system 22 are able to rotate with rotation of the extension arm 26 about the ceiling attachment member 24. As illustrated in FIG. 5, the second section 52 of the cabling system 22 enters the hollow tube 82 of the extension arm 26 through a cabling entrance 116 in the hollow tube 82 adjacent the spindle receiving block 86 at the proximal end 80 of the extension arm 26. A cosmetic and protective cover 118 covers a bottom of the proximal end 80 of the extension arm 26, with the cosmetic and protective cover 118 being connected to a bottom of the hollow tube 82 in order to cover the cabling entrance 116 and also being connected to a bottom of the spindle receiving block 86 to protect a bottom of the spindle receiving block 86, the infinite rotation fiber optic and slip ring joint 14 at the first infinite rotation joint 28, the disc shaped spanner nut 112, and the central axis spindle 50. The cosmetic and protective cover 118 protects the second section 52 of the cabling system 22 connected to the infinite rotation fiber optic and slip ring joint 14 at the first infinite rotation joint 28 and hides the second section 52 of the cabling system 22 from exposure.

Figure 6:
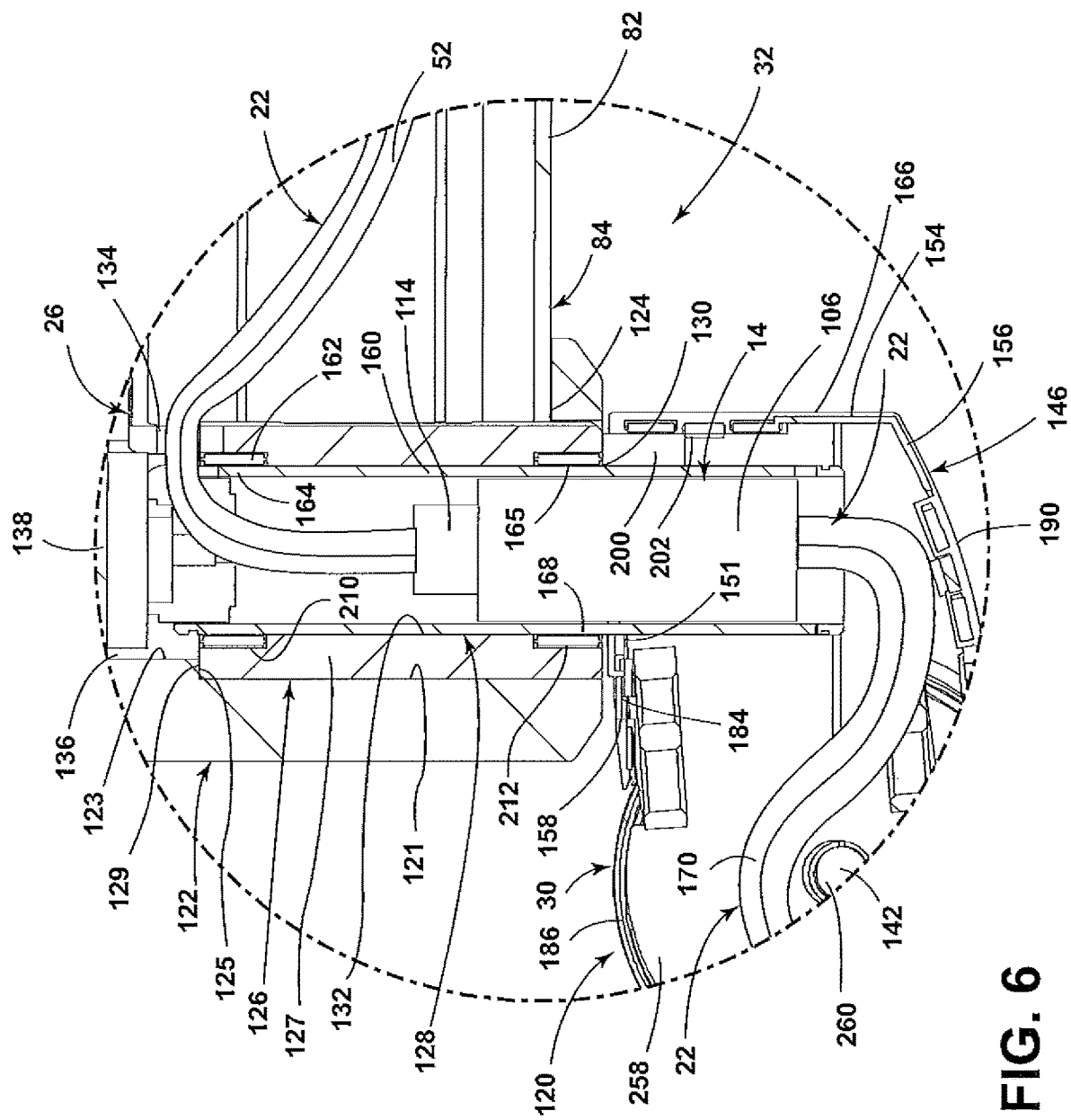
FIG. 6 is an enlarged cross-sectional view of a second infinite rotation joint of the suspension arm assembly according to the present invention taken from the circle VI of FIG. 4.

The illustrated second section 52 of the cabling system 22 extends through the extension arm 26 and is connected to a second one of the infinite rotation fiber optic and slip ring joints 14 at the second infinite rotation joint 32. The second infinite rotation joint 32 includes an intersection of the extension arm 26 at the distal end 84 thereof and a proximal end 120 of the load counterbalancing spring arm 30. The illustrated extension arm 26 includes a circular pivot tube receiving block 122 at the distal end 84 thereof, with the circular pivot tube receiving block 122 being connected to the hollow tube 82 of the extension arm 26. The circular pivot tube receiving block 122 includes a side tube receiving bore 124 receiving the hollow tube 82 therein for fixing the hollow tube 82 to the circular pivot tube receiving block 122. As illustrated in FIG. 6, the circular pivot tube receiving block 122 includes a stepped vertically oriented circular bearing tube receiving hole 126 extending therethrough. The stepped vertically oriented circular bearing tube receiving hole 126 includes a smaller diameter lower portion 121, a larger diameter upper portion 123 and a step 125 between the smaller diameter lower portion 121 and the larger diameter upper portion 123. A tubular sleeve 127 is located in the smaller diameter lower portion 121 and a top surface 129 of the tubular sleeve 127 abuts the step 125. As illustrated in FIG. 6, the hollow tube 82 is inserted into the side tube receiving bore 124 until the hollow tube 82 abuts the exterior surface of the tubular sleeve 127.

In the illustrated example, the tubular sleeve 127 is configured to receive a bearing tube 128 of the load counterbalancing spring arm 30 therein for connecting the load counterbalancing spring arm 30 to the extension arm 26. An interior surface of the tubular sleeve 127 defines a circular inner bearing surface 132 within the circular pivot tube receiving block 122. As illustrated in FIG. 6, an access area 134 is located in the circular pivot tube receiving block 122 above the tubular sleeve 127 for allowing the second section 52 of the cabling system 22 to pass from the hollow tube 82 and into the circular pivot tube receiving block 122. It is contemplated that the circular pivot tube receiving block 122 could have an open top 136 covered by a removable cover 138. The tubular sleeve 127 has an open bottom area 130 for receiving the bearing tube 128 of the load counterbalancing spring arm 30 therein.

The illustrated load counterbalancing spring arm 30 is configured to rotate about a second vertical axis 131 at the second infinite rotation joint 32 and a third vertical axis 133 at the third infinite rotation joint 34 (see FIG. 2). The load counterbalancing spring arm 30 is also configured to allow the third infinite rotation joint 34 to move vertically relative to the second infinite rotation joint 32. The load counterbalancing spring arm 30 includes a proximal knuckle member 146, a central member 140 and a distal knuckle member 148. The proximal knuckle member 146 has the bearing tube 128 extending therefrom for connecting the proximal knuckle member 146, and thereby the load counterbalancing spring arm 30, to the extension arm 26. The proximal knuckle member 146 also includes the second vertical axis 131 extending therethrough. The proximal knuckle member 146 is pivotally connected to the central member 140 to allow the central member 140 to pivot about a first horizontal axis 142. The central member 140 is also pivotally connected to the distal knuckle member 148 to allow the central member 140 to pivot about a second horizontal axis 144. The distal knuckle member 148 also includes the third vertical axis 133 extending therethrough. The distal knuckle member 148 is connected to the wired medical unit 16 as discussed in more detail below.

In the illustrated example, the proximal knuckle member 146 has the bearing tube 128 extending therefrom for connecting the proximal knuckle member 146 to the extension arm 26. The proximal knuckle member 146 includes a U-shaped side wall 154, a bottom wall 156 and a top wall 158, with the bearing tube 128 extending through an opening 151 in the top wall 158. The U-shaped side wall 154 includes a curved wall section 166 below the circular pivot tube receiving block 122 and a pair of stepped side wall sections 180 extending from the curved wall section 166 to define an open end opposite the curved wall section 166. Each of the stepped side wall sections 180 include a circular recessed area at a terminal end thereof for accepting disc projections 182 of the central member 140 as discussed in more detail below. The top wall 158 includes a substantially flat portion 184 connected to a top of the U-shaped side wall 154 and an arcuate portion 186 connected to the top of the circular recessed areas of the U-shaped side wall 154. The bottom wall 156 includes a curved section 190 connected to a bottom of the U-shaped side wall 154 and an arcuate portion 192 connected to the bottom of the circular recessed areas of the U-shaped side wall 154. As illustrated in FIG. 6, the bearing tube 128 extends upwardly out of the opening 151 in the flat portion 184 of the top wall 158 and directly into the tubular sleeve 127 of the circular pivot tube receiving block 122. A fixing projection 200 extends from an inside face 202 of the U-shaped side wall 154 to connect the bearing tube 128 to the proximal knuckle member 146.

The illustrated bearing tube 128 of the load counterbalancing spring arm 30 is inserted into the open bottom area 130 of the tubular sleeve 127 of the circular pivot tube receiving block 122 of the extension arm 26 to connect the load counterbalancing spring arm 30 to the extension arm 26. The bearing tube 128 includes a bearing cylinder 160, an upper bearing ring 162 connected to an upper area 164 of the bearing cylinder 160 and a middle bearing ring 165 connected to a middle area 168 of the bearing cylinder 160 directly above the top wall 158 of the proximal knuckle member 146. The tubular sleeve 127 includes an upper circular recess 210 receiving the upper bearing ring 162 therein and a lower circular recess 212 receiving the middle bearing ring 165 therein for allowing the bearing tube 128, and thereby the load counterbalancing spring arm 30, to rotate relative to the extension arm 26. The wired medical unit 16 is thereby allowed to rotate about the second vertical axis 131 at the second infinite rotation joint 32.

In the illustrated example, one of the infinite rotation fiber optic and slip ring joints 14 at the second infinite rotation joint 32 is connected to the second section 52 of the cabling system 22 and a third section 170 of the cabling system 22 extending through the load counterbalancing spring arm 30 as discussed in more detail below. The stator 106 of the infinite rotation fiber optic and slip ring joint 14 at the second infinite rotation joint 32 is fixed to the bearing tube 128 by fasteners (or any other connection method) such that the stator 106 of the infinite rotation fiber optic and slip ring joint 14 at the second infinite rotation joint 32 is stationary relative to the load counterbalancing spring arm 30. Likewise, the rotor 114 of the infinite rotation fiber optic and slip ring joint 14 at the second infinite rotation joint 32 is allowed to rotate relative to the stator 106.

Figure 4:
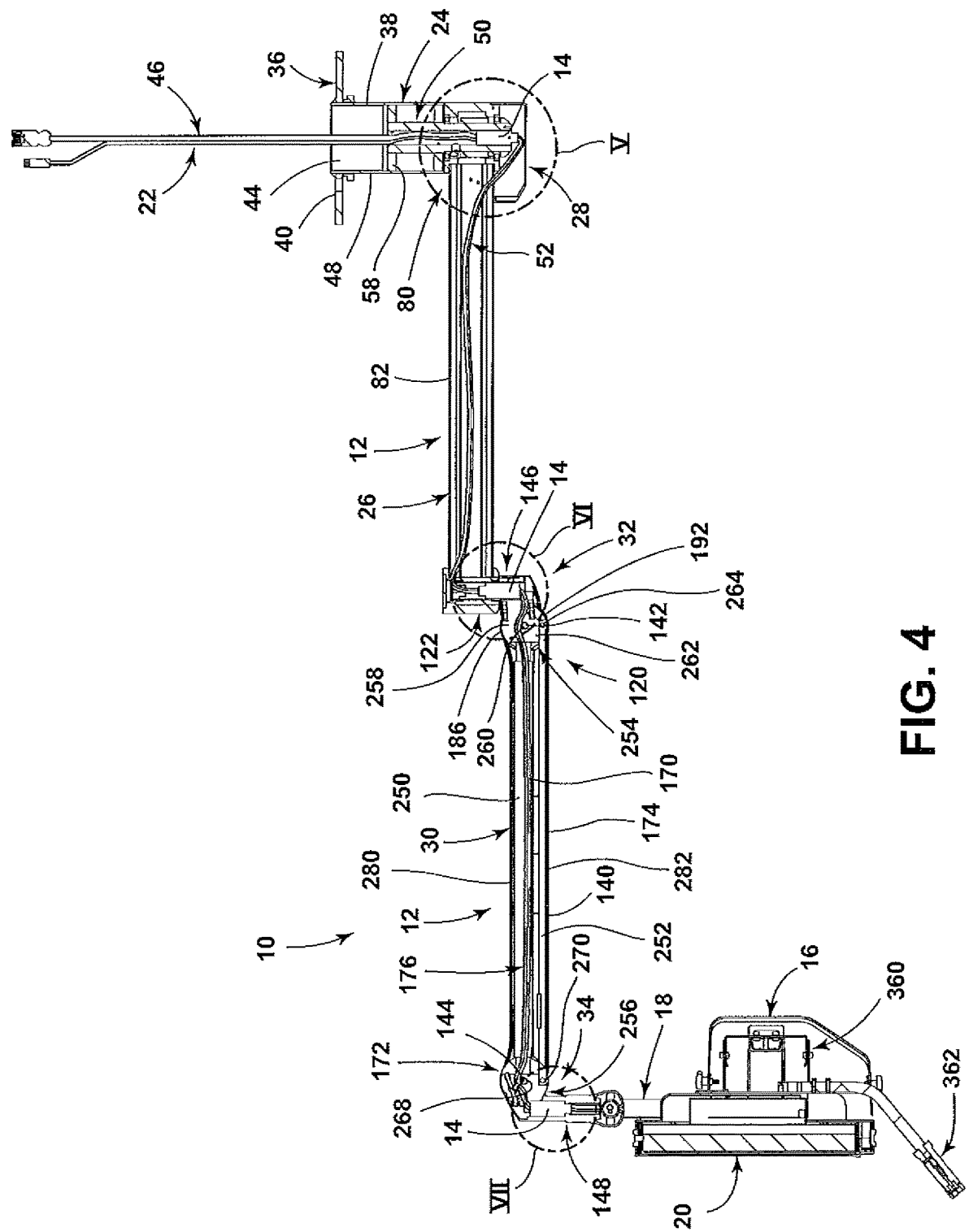
FIG. 4 is a cross-sectional view of the suspension arm assembly according to the present invention.
Figure 7:
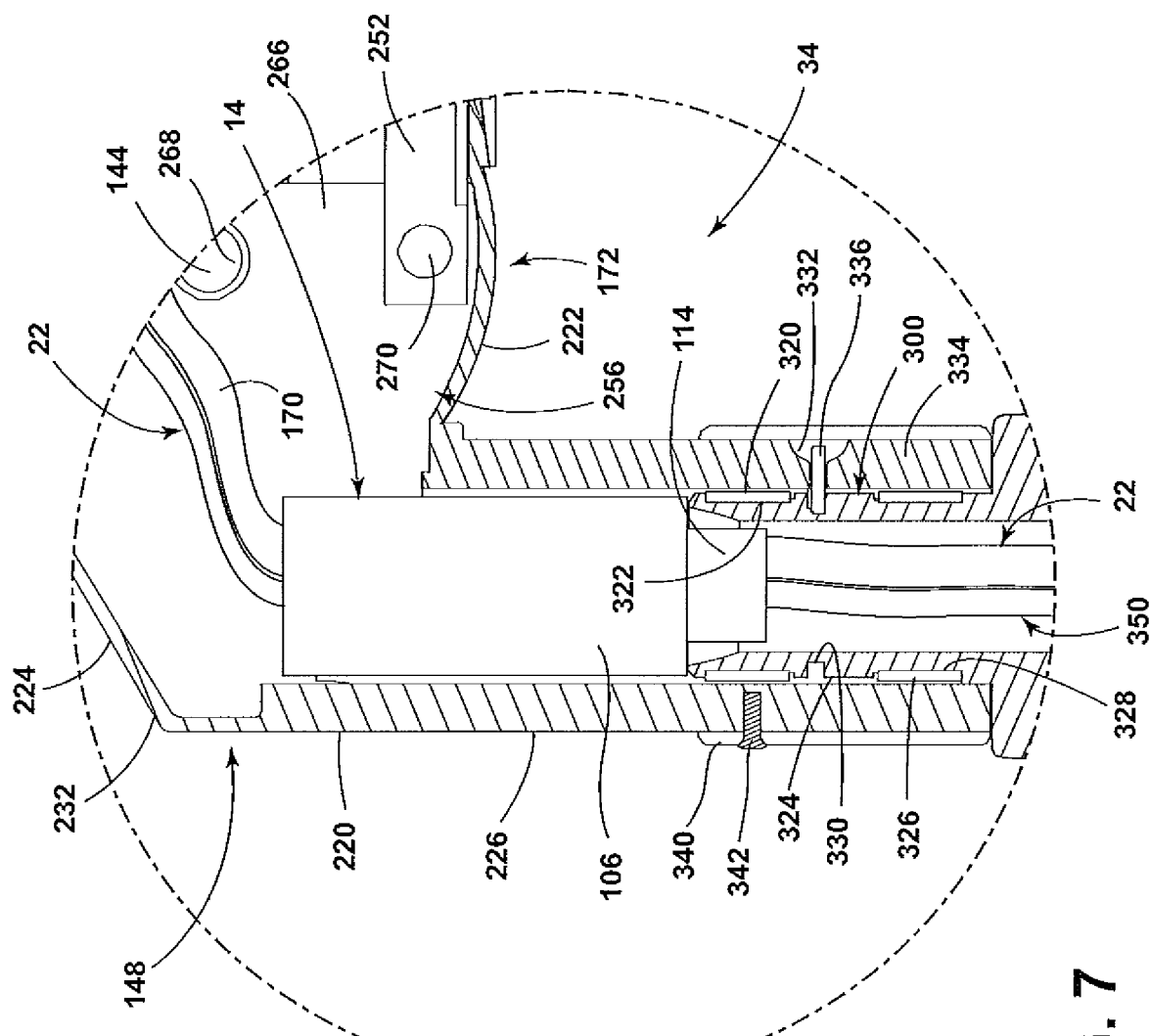
FIG. 7 is an enlarged cross-sectional view of a third infinite rotation joint of the suspension arm assembly according to the present invention taken from the circle VII of FIG. 4.

As illustrated in FIGS. 4, 6 and 7, the third section 170 of the cabling system 22 extends through the central member 140 of the load counterbalancing spring arm 30 and is connected to a third one of the infinite rotation fiber optic and slip ring joints 14 at the third infinite rotation joint 34. The third infinite rotation joint 34 includes an intersection of the load counterbalancing spring arm 30 at the distal end 172 thereof and the wired medical unit 16. The central member 140 of the load counterbalancing spring arm 30 is pivotally connected to the proximal knuckle member 146 at the first horizontal axis 142 to allow the wired medical unit 16 to rotate about the first horizontal axis 142. The central member 140 is also pivotally connected to the distal knuckle member 148 at the second horizontal axis 144 to allow the wired medical unit 16 to rotate about the second horizontal axis 144.

The illustrated load counterbalancing spring arm 30 is configured to have the central member 140 rotate simultaneously about the proximal knuckle member 146 and the distal knuckle member 148. The central member 140 includes an outer shell 174 having a substantially rectangular cross-sectional shape. A parallel pair of the disc projections 182 extend from each end of the outer shell 174. A parallelogram connection assembly 176 extends through the outer shell 174 and is connected to both the proximal knuckle member 146 and the distal knuckle member 148 to allow the central member 140 to rotate simultaneously about the proximal knuckle member 146 and the distal knuckle member 148.

In the illustrated example, the distal knuckle member 148 connects the load counterbalancing spring arm 30 to the wired medical unit 16. The distal knuckle member 148 includes a U-shaped side wall 220, a bottom wall 222 and a top wall 224, with a down tube 226 extending downwardly from the bottom wall 222 for connection to the display support assembly 18 of the wired medical unit 16. The U-shaped side wall 220 includes a curved wall section 228 coextensive with the down tube 226 and a pair of stepped side wall sections 230 extending from the curved wall section 228 to define an open end opposite the curved wall section 228. Each of the stepped side wall sections 230 include a circular recessed area at a terminal end thereof for accepting disc projections 182 of the central member 140 as discussed in more detail below. The top wall 224 includes an angled portion 232 connected to a top of the U-shaped side wall 220 and an arcuate portion 234 connected to the top of the circular recessed areas of the U-shaped side wall 220. The bottom wall 222 is arcuate and is connected to a bottom of the U-shaped side wall 220.

The illustrated parallelogram connection assembly 176 extends between and is connected to the proximal knuckle member 146 and the distal knuckle member 148. The parallelogram connection assembly 176 includes an upper rod 250, a lower rod 252, a proximal knuckle connection 254 and a distal knuckle connection 256. The proximal knuckle connection 254 includes a pair of parallel plates 258 extending between the arcuate portion 186 of the top wall 158 and the arcuate portion 192 of the bottom wall 156 of the proximal knuckle member 146. The upper rod 250 is located between the parallel plates 258 and pivotally connected thereto by a pivot pin 260 located at the first horizontal axis 142 to allow the upper rod 250 to pivot about the first horizontal axis 142. The lower rod 252 is pivotally connected to an outside face 262 of one of the parallel plates 258 by a pivot pin 264. Like the proximal knuckle connection 254, the distal knuckle connection 256 includes a pair of parallel plates 266 extending between the arcuate portion 234 of the top wall 224 and the bottom wall 222 of the distal knuckle member 148. The upper rod 250 is located between the parallel plates 266 and pivotally connected thereto by a pivot pin 268 located at the second horizontal axis 144 to allow the upper rod 250 to pivot about the second horizontal axis 144. The lower rod 252 is pivotally connected to an outside face 262 of one of the parallel plates 266 by a pivot pin 270.

In the illustrated example, the parallelogram connection assembly 176 allows the second horizontal axis 144 to move vertically relative to the first horizontal axis 142. As the distal knuckle member 148 is lowered, the upper rod 250 will pivot about the pivot pin 260 located at the first horizontal axis 142, which will also force the lower rod 252 to pivot about the pivot pin 264 at the proximal knuckle member 146. Because the upper rod 250 and the lower rod 252 of the parallelogram connection assembly 176 form a parallelogram with the parallel plates 258 in the proximal knuckle member 146 and the parallel plates 266 in the distal knuckle member 148, the distal knuckle member 148 will not rotate as the distal knuckle member 148 is lowered (that is, a line between the pivot pin 260 and the pivot pin 264 in the proximal knuckle member 146 will remain substantially parallel to a line between the pivot pin 268 and the pivot pin 268 in the distal knuckle member 148, with both lines remaining substantially vertical). As is well known to those skilled in the art, a spring can be located within the central member 140 (e.g., partially surrounding the upper rod 250) to maintain the parallelogram connection assembly 176 in a selected rotated position.

The illustrated central member 140 covers the pivot areas of the load counterbalancing spring arm 30. The outer shell 174 of the central member 140 includes a top wall 280 that rides on the arcuate portion 186 of the top wall 158 of the proximal knuckle member 146 and the arcuate portion 234 of the top wall 224 and the bottom wall 222 of the distal knuckle member 148 during lowering and raising of the load counterbalancing spring arm 30. Likewise, the outer shell 174 of the central member 140 includes a bottom wall 282 that rides on the arcuate portion 192 of the bottom wall 156 of the proximal knuckle member 146 and the bottom wall 222 of the distal knuckle member 148 during lowering and raising of the load counterbalancing spring arm 30. Each end of the side walls 284 of the outer shell 174 of the central member 140 have one of the disc projections 182 extending therefrom. The disc projections 182 cover the circular recessed area at the terminal ends of the stepped side wall sections 180 of the U-shaped side wall 154 of the proximal knuckle member 146 to form a cosmetic joint. The disc projections 182 also cover the circular recessed area of the pair of stepped side wall sections 230 of the U-shaped side wall 220 of the distal knuckle member 148 to form a cosmetic joint.

In the illustrated example, the distal knuckle member 148 connects the load counterbalancing spring arm 30 to the wired medical unit 16. The down tube 226 of the distal knuckle member 148 receives a bushing cylinder 300 of the display support assembly 18 therein to connect the distal knuckle member 148, and thereby the load counterbalancing spring arm 30, to the display support assembly 18. The display support assembly 18 includes an inverted U-shaped frame member 302, an arm connection assembly 304 connected to a top of the inverted U-shaped frame member 302 and a pair of display pivot brackets 306. The arm connection assembly 304 includes a split sleeve 308 that surrounds the top of the inverted U-shaped frame member 302, with the bushing cylinder 300 extending upwardly from a center of the split sleeve 308. The bushing cylinder 300 includes an upper cylindrical bushing 320 located in an upper bushing channel 322 in an outside surface 324 of the bushing cylinder 300 and a lower cylindrical bushing 326 located in a lower bushing channel 328 in the outside surface 324 of the bushing cylinder 300. A pin slot 330 extends around the perimeter of the bushing cylinder 300 between the upper bushing channel 322 and the lower bushing channel 328.

The illustrated wired medical unit 16 is connected to the distal knuckle member 148 of the load counterbalancing spring arm 30 by inserting the bushing cylinder 300 of the display support assembly 18 into the down tube 226 of the distal knuckle member 148. As illustrated in FIG. 7, the down tube 226 of the distal knuckle member 148 has a radial pin opening 332 extending through a wall 334 of the down tube 226. When the bushing cylinder 300 of the display support assembly 18 is fully inserted into the down tube 226 of the distal knuckle member 148, the radial pin opening 332 in the wall 334 of the down tube 226 is aligned with the pin slot 330 in the bushing cylinder 300. A yoke retaining clip 336 extends through the radial pin opening 332 and into the pin slot 330 in the bushing cylinder 300 to connect the wired medical unit 16 to the distal knuckle member 148. The yoke retaining clip 336 also allows the wired medical unit 16 to rotate about the distal knuckle member 148 at the third vertical axis 133. Once the yoke retaining clip 336 is inserted into the radial pin opening 332 and the pin slot 330, a cylindrical retaining clip sleeve 340 surrounding the down tube 226 is slid downward to cover the radial pin opening 332 in the wall 334 of the down tube 226 to lock the yoke retaining clip 336 in position. A fastener 342 can be inserted through the cylindrical retaining clip sleeve 340 and into the down tube 226 to lock the cylindrical retaining clip sleeve 340 in position.

In the illustrated example, one of the infinite rotation fiber optic and slip ring joints 14 at the third infinite rotation joint 34 is connected to the third section 170 of the cabling system 22 and a fourth section 350 of the cabling system 22 extending to the display monitor 20. The stator 106 of the infinite rotation fiber optic and slip ring joint 14 at the third infinite rotation joint 34 is fixed to the down tube 226 of the distal knuckle member 148 by fasteners (or any other connection method) such that the stator 106 of the infinite rotation fiber optic and slip ring joint 14 at the third infinite rotation joint 34 is stationary relative to the load counterbalancing spring arm 30. Likewise, the rotor 114 of the infinite rotation fiber optic and slip ring joint 14 at the third infinite rotation joint 34 is allowed to rotate relative to the stator 106.

The illustrated fourth section 350 of the cabling system 22 extends through the down tube 226 of the distal knuckle member 148 of the load counterbalancing spring arm 30, the bushing cylinder 300 of the arm connection assembly 304, the inverted U-shaped frame member 302, and to the display pivot brackets 306. As illustrated in FIGS. 1-4, the display pivot brackets 306 are connected to a display frame and cable shield 360 holding the display monitor 20 and allow the display monitor 20 to pivot about the display pivot brackets 306. The display frame and cable shield 360 can have a handle 362 to assist in positioning the display monitor 20 to a desired position. It is contemplated that the handle 362 can be removable for sterilization and/or can have a removable/replaceable sterilizable cover.

The illustrated cabling system 22 provides power and information to the wired medical unit 16 through the display support assembly 18. It is contemplated that each of the infinite rotation fiber optic and slip ring joints 14 can transmit any combination of the following: digital data through a fiber optic connection, digital or analog data through at least one coaxial cable connection, digital or analog data through at least one serial data connection, low voltage power through at least one low voltage power connection, AC power through at least one AC power connection, and a ground wire connection.

Figure 8:
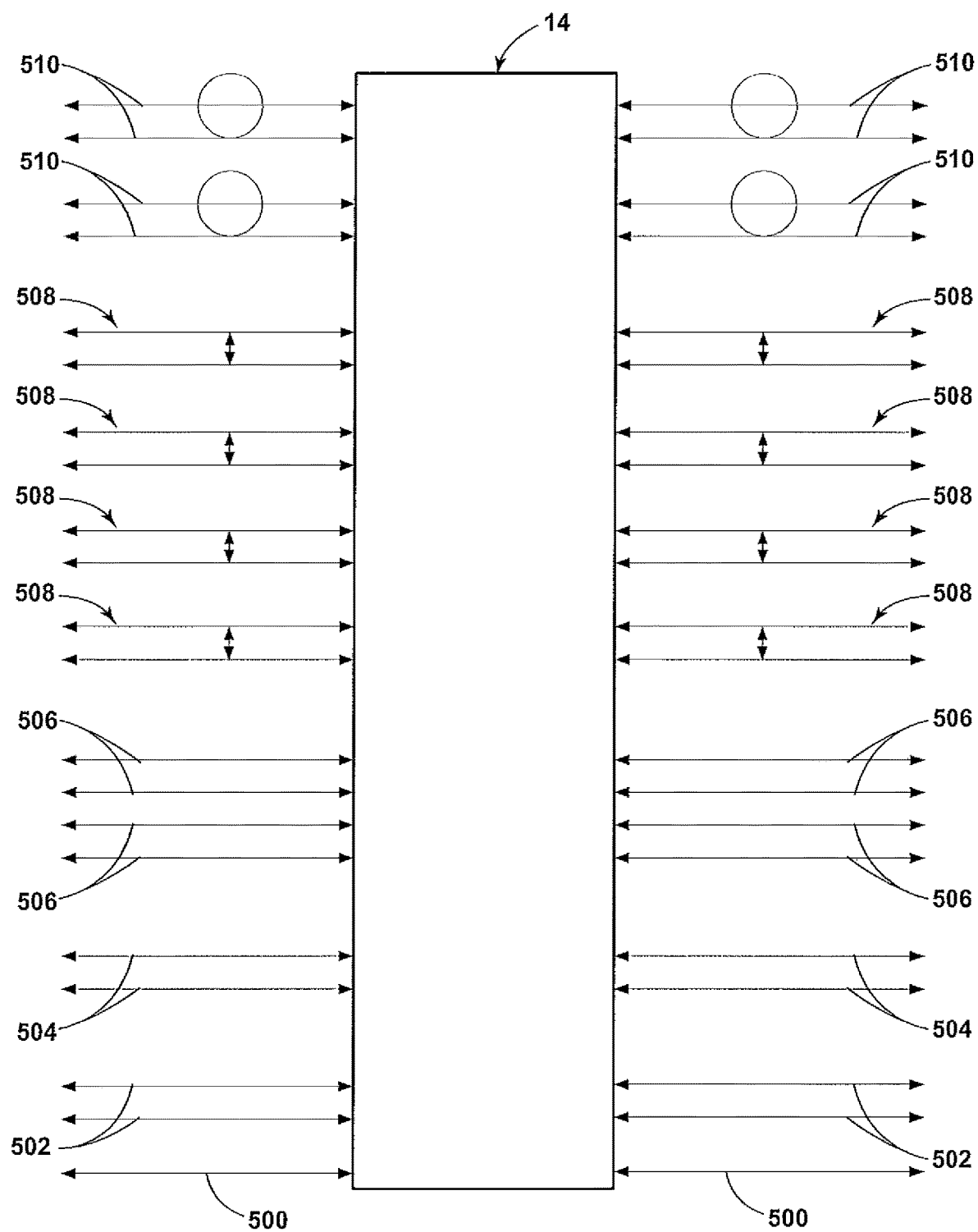
FIG. 8 is a schematic view of the data and power communications across an infinite rotation fiber optic and slip ring rotary joint according to the present invention.

FIG. 8 illustrates the power and information transmitted through the cabling system 22 and each of the infinite rotation fiber optic and slip ring joints 14 of the illustrated embodiment. The illustrated cabling system 22 includes a fiber optic cable 500 leading into and out of each infinite rotation fiber optic and slip ring joint 14, a pair of ground wires 502 leading into and out of each infinite rotation fiber optic and slip ring joint 14, a pair of AC power wires 504 leading into and out of each infinite rotation fiber optic and slip ring joint 14, four low voltage wires 506 leading into and out of each infinite rotation fiber optic and slip ring joint 14, four twisted pairs of serial data wires 508 leading into and out of each infinite rotation fiber optic and slip ring joint 14 and four coaxial cables 510 leading into and out of each infinite rotation fiber optic and slip ring joint 14. However, it is contemplated that the cabling system 22 could have more or less of the wires and cables outlined above.

The following chart lists examples of the cables and wires leading into and out of each infinite rotation fiber optic and slip ring joint 14:

| Function: | Cable type: | Size: | Type: | Volts: | Amps: | Data type: |
|---|---|---|---|---|---|---|
| Video and Audio Data transmission | Fiber optic | 50 μm broadband with a 3 mm jacket | | | | HD-SDI, DVI, HDMI, any HD signals, any SD signals, Ethernet, network and other data |
| Video and Audio Data transmission | Coaxial cable | | RG-179 | 10 | 100 mA max | |
| Serial Data transmission | Serial Cable in Twisted Pairs | 26-28 AWG | | 10 | 100 mA max | RS-232, RS-485, CAN, etc. |
| Low Voltage Power | Cu or Al wire | 26-28 AWG | | 28 max | 1000 mA max | |
| AC Power | Cu or Al wire | 16-18 AWG | | 120-240 VAC | 10 A | |
| Ground | Cu or Al wire | 18 AWG | | 120-240 VAC | 10 A | |

It is contemplated that the fiber optic cable 500 can be single mode or multimode and can have at least 10 Gb of bandwidth. The coaxial cables 510 can have an impedance of 75Ω and can be a coaxial cable sold as part number MOGAMI W3351 by MIT Inc. of Tokyo, Japan. The AC power wires 504 can be a power line sold as part number 3516/19 by Weico Wire & Cable Inc. of Edgewood, N.Y.

In the illustrated example, the infinite rotation fiber optic and slip ring joints 14 (FIGS. 9A-11) transmit all of the data and power through the first infinite rotation joint 28, the second infinite rotation joint 32 and the third infinite rotation joint 34. The infinite rotation fiber optic and slip ring joint 14 includes a slip ring housing 520 and a fiber optic rotary joint 522 within the slip ring housing 520. The slip ring housing 520 includes the rotor 114 and the stator 106. The stator 106 includes an exterior stator cylinder 524 having a rotor end wall 526 and an exit end wall 528. An internal stator cylinder 530 substantially co-axial with the exterior stator cylinder 524 is connected to the exit end wall 528. A wiring area 532 is defined between the exterior stator cylinder 524 and the internal stator cylinder 530. A stator and fiber optic rotary joint area 534 is defined within the internal stator cylinder 530.

The illustrated rotor 114 includes an exterior cylindrical portion 536 extending from the rotor end wall 526 of the stator 106 and an interior portion 538 located within the stator and fiber optic rotary joint area 534 of the stator 106. The exterior cylindrical portion 536 defines a tubular housing 540 having an entrance end 535 opposite the stator 106. The fiber optic cable 500 enters the entrance end 535 of the exterior cylindrical portion 536 of the rotor 114 through a center portion thereof. It is contemplated that the fiber optic cable 500 outside of the rotor 114 can have a connector 542 (e.g., a SC, LC, FC, ST, SMA or pigtail type connector) for connecting the fiber optic cable 500 passing through the infinite rotation fiber optic and slip ring joint 14 to the fiber optic cable 500 of the first section 46, the second section 52, the third section 170 or the fourth section 350 of the cabling system 22. It is also contemplated that the fiber optic cable 500 can run uninterrupted up to and between the infinite rotation fiber optic and slip ring joints 14. The ground wires 502, the AC power wires 504, the low voltage wires 506, the twisted pairs of serial data wires 508 and the coaxial cables 510 enter the entrance end 535 of the exterior cylindrical portion 536 of the rotor 114 adjacent a peripheral edge 544 of the entrance end 535.

The illustrated ground wires 502, the AC power wires 504, the low voltage wires 506, the twisted pairs of serial data wires 508 and the coaxial cables 510 entering the exterior cylindrical portion 536 of the rotor 114 are connected to a center rotating shaft 546 made up of a plurality of individual contact rings 551 and forming the interior portion 538 of the rotor 114. Each of the ground wires 502, the AC power wires 504, the low voltage wires 506, the serial data wires 508 and the coaxial cables 510 are connected to one of the individual contact rings 551 of the center rotating shaft 546. As illustrated in FIGS. 10 and 11, each of the individual contact rings 551 are separate by an insulation ring 553 to prevent power or data from crossing over to adjacent individual contact rings 551. Each of the individual contact rings 551 include a plurality of circumferential grooves 560 for receiving contact members 562 of the stator 106 as discussed in more detail below. It is contemplated that the individual contact rings 551 transferring power can be located closer to the exterior cylindrical portion 536 of the rotor 114, can have larger diameters and can have adjacent insulation rings 553 with a greater thickness (see FIG. 10) than the individual contact rings 551 transferring data (see FIG. 11). The center rotating shaft 546 includes a plurality of terminal end openings 564 for accepting fasteners 566 therein to connect a rotor portion 568 of the fiber optic rotary joint 522 to the center rotating shaft 546. The center rotating shaft 546 also includes a circumferential groove 548 at an end thereof opposite the exterior cylindrical portion 536 of the rotor 114. A bearing ring 550 is located within the circumferential groove 548 to support the center rotating shaft 546 and to allow the center rotating shaft 546 to rotate within the stator 106.

Figure 9A:
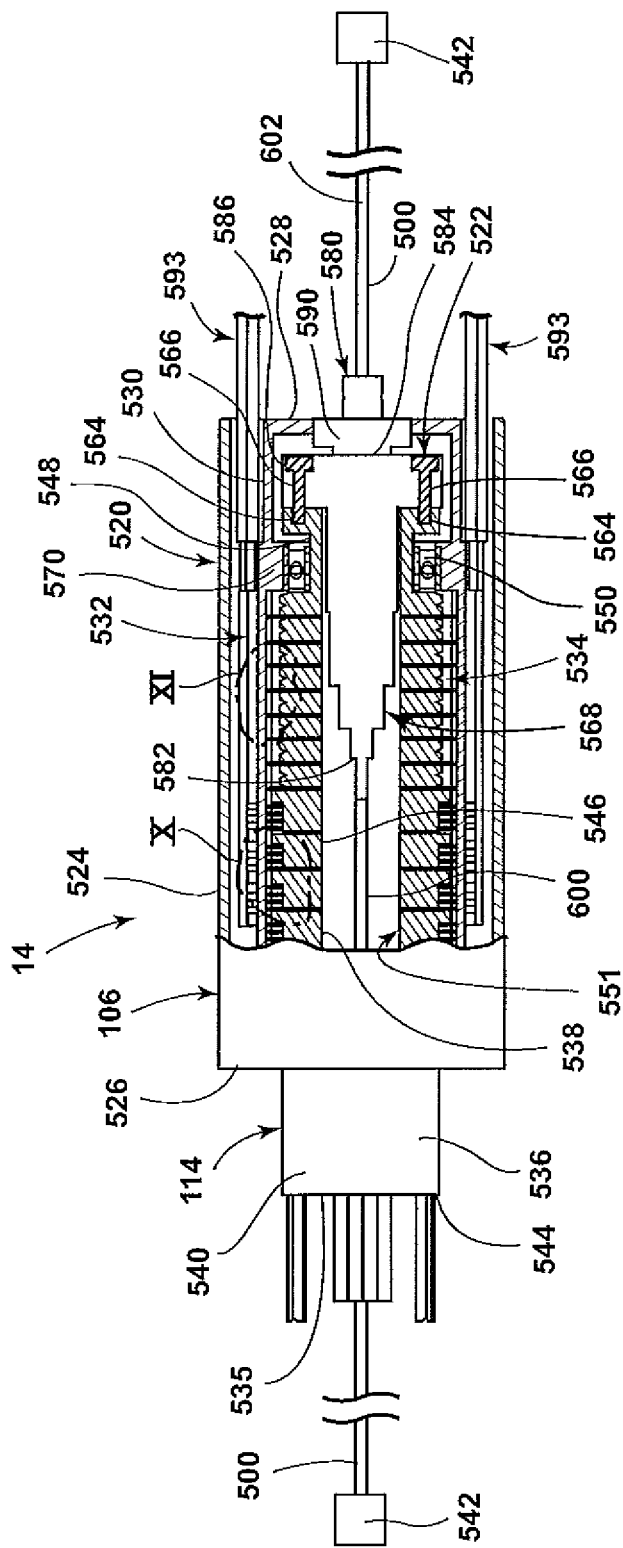
FIG. 9A is a partial cross-sectional side view of a infinite rotation fiber optic and slip ring rotary joint according to the present invention.
Figure 9C:
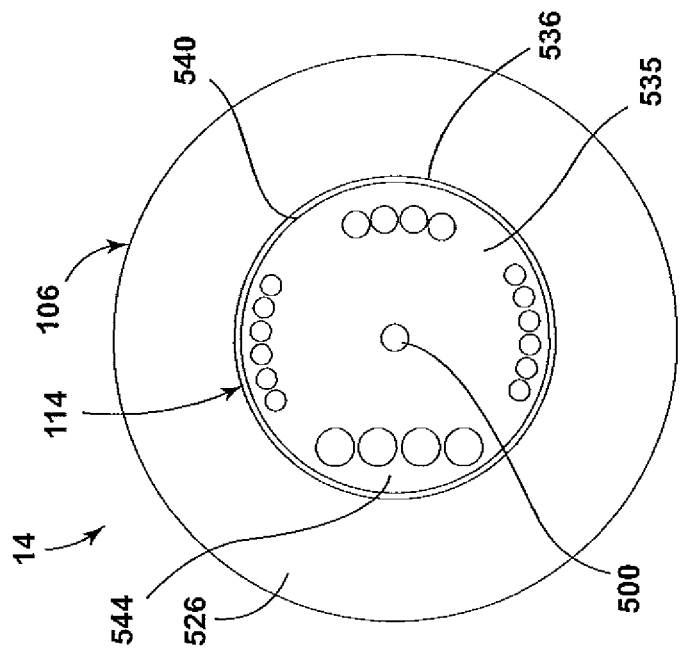
FIG. 9C is a second end view of the infinite rotation fiber optic and slip ring rotary joint according to the present invention.
Figure 9B:
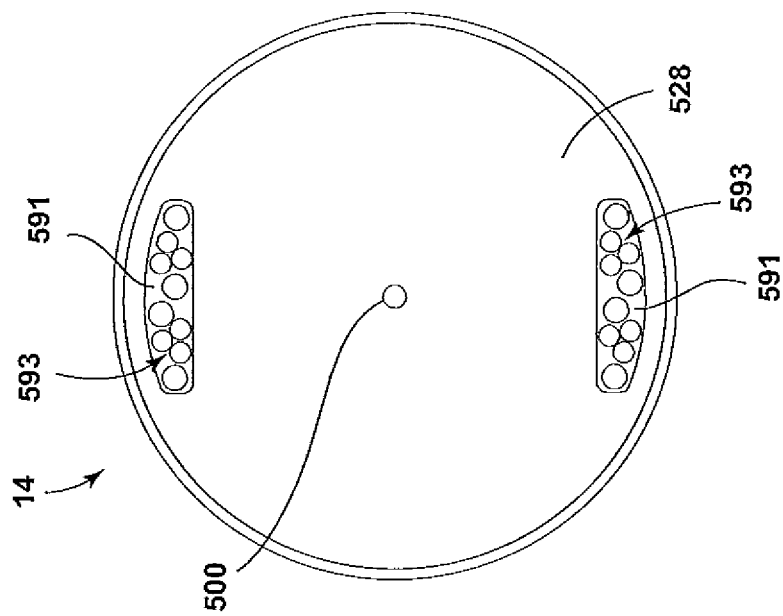
FIG. 9B is a first end view of the infinite rotation fiber optic and slip ring rotary joint according to the present invention.

The illustrated stator 106 includes a portion of the rotor 114 therein to receive data and power from the rotor 114. The stator 106 includes the exterior stator cylinder 524 having the rotor end wall 526 and the exit end wall 528, with the internal stator cylinder 530 extending substantially co-axial with the exterior stator cylinder 524 from the exit end wall 528. The internal stator cylinder 530 includes an enlarged abutment area 570 abutting the bearing ring 550 located within the circumferential groove 548 of the center rotating shaft 546 of the rotor 114 to allow the center rotating shaft 546 and the rotor 114 to rotate relative to the stator 106. The contact members 562 extend through the internal stator cylinder 530 (see FIGS. 10 and 11) and make contact with the plurality of circumferential grooves 560 in the individual contact rings 551 of the internal stator cylinder 530. The contact members 562 on the outside surface of the internal stator cylinder 530 are engaged with the ground wires 502, the AC power wires 504, the low voltage wires 506, the twisted pairs of serial data wires 508 and the coaxial cables 510 exiting the stator 106. As illustrated in FIGS. 9A and 9B, the ground wires 502, the AC power wires 504, the low voltage wires 506, the twisted pairs of serial data wires 508 and the coaxial cables 510 exit the exit end wall 528 through openings 591 located adjacent the periphery of the exit end wall 528 in wiring groups 593.

The power and data is transferred from the ground wires 502, the AC power wires 504, the low voltage wires 506, the twisted pairs of serial data wires 508 and the coaxial cables 510 entering the infinite rotation fiber optic and slip ring joint 14 to the ground wires 502, the AC power wires 504, the low voltage wires 506, the twisted pairs of serial data wires 508 and the coaxial cables 510 exiting the infinite rotation fiber optic and slip ring joint 14. As discussed above, the power and data is first transferred from the ground wires 502, the AC power wires 504, the low voltage wires 506, the twisted pairs of serial data wires 508 and the coaxial cables 510 entering the infinite rotation fiber optic and slip ring joints 14 to the individual contact rings 551 of the center rotating shaft 546. The contact members 562 extending through the internal stator cylinder 530 of the stator 106 make contact with the plurality of circumferential grooves 560 in the individual contact rings 551 of the internal stator cylinder 530 to transfer the power and data. It is contemplated that the contact members 562 can be brushes (e.g., graphite particles dispersed in a matrix of silver with the individual contact rings 551 also being made of silver, gold alloys forming a mono or multi-filament brush with the individual contact rings 551 also be made of a gold based alloy, etc.), a flexure ring that bridges the outer ring and the inner ring and that moves like balls in a ball bearing, or liquid mercury. The power and data is thereafter transferred through the contacts to the ground wires 502, the AC power wires 504, the low voltage wires 506, the twisted pairs of serial data wires 508 and the coaxial cables 510 entering the infinite rotation fiber optic and slip ring joint 14 to the ground wires 502, the AC power wires 504, the low voltage wires 506, the twisted pairs of serial data wires 508 and the coaxial cables 510 exiting the infinite rotation fiber optic and slip ring joint 14. While power and data is discussed above and travelling only in one direction from the rotor 114 to the stator 106, the power and data can travel in both directions through the infinite rotation fiber optic and slip ring joint 14. Moreover, the infinite rotation fiber optic and slip ring joint 14 is capable of being orientated in any direction (e.g., either the stator 106 or the rotor 114 being located first in the direction of data and power in the cabling system 22 to the wired medical unit 16). The fiber optic cable 500 exits the exit end wall 528 of the stator 106 through a center portion thereof. It is contemplated that the fiber optic cable 500 outside of the stator 106 can have the connector 542 (e.g., a SC, LC, FC, ST, SMA or pigtail type connector) for connecting the fiber optic cable 500 passing through the infinite rotation fiber optic and slip ring joint 14 to the fiber optic cable 500 of the first section 46, the second section 52, the third section 170 or the fourth section 350 of the cabling system 22. It is also contemplated that the fiber optic cable 500 can run uninterrupted up to and between the infinite rotation fiber optic and slip ring joints 14.

In the illustrated example, data also passes through the infinite rotation fiber optic and slip ring joint 14 through the fiber optic rotary joint 522 within the slip ring housing 520. The fiber optic rotary joint 522 includes the rotor portion 568 and a stator portion 580. The rotor portion 568 includes increasing larger diameter areas having an entrance end 582 and a stator connection end 584. A largest diameter area 586 of the rotor portion 568 includes the fasteners 566 extending therethrough and into the terminal end openings 564 of the center rotating shaft 546 of the rotor 114 to force the rotor portion 568 of the fiber optic rotary joint 522 to rotate with the remainder of the rotor 114. The stator portion 580 of the fiber optic rotary joint 522 is rotatably connected to the rotor portion 568. The stator portion 580 of the fiber optic rotary joint 522 includes a head 590 connected to the exit end wall 528 of the exterior stator cylinder 524 of the stator 106 such that the stator portion 580 of the fiber optic rotary joint 522 remains stationary with the remainder of the stator 106.

The illustrated fiber optic cable 500 enters the rotor 114 through the entrance end 535 of the tubular housing 540 of the exterior cylindrical portion 536 of the rotor 114 and exits the stator 106 through the head 590 of the stator portion 580 of the fiber optic rotary joint 522. The fiber optic cable 500 is split within the fiber optic rotary joint 522 such that a first portion 600 of the fiber optic cable 500 within the fiber optic rotary joint 522 rotates with the rotor portion 568 of the fiber optic rotary joint 522 and a second portion 602 of the fiber optic cable 500 within the fiber optic rotary joint 522 remains stationary with the stator portion 580 of the fiber optic rotary joint 522. The data is transferred from the first portion 600 of the fiber optic cable 500 to the second portion 602 of the fiber optic cable 500 in a manner well known to those skilled in the art. The fiber optic rotary joint 522 can be the fiber optic rotary joint disclosed in U.S. Patent Application Publication No. 2009/0226131 entitled "FIBER OPTIC ROTARY COUPLER," the entire contents of which are hereby incorporated herein by reference. The fiber optic rotary joint 522 can also be a fiber rotary joint sold as part number MJXX-131-50T-STD or MJXX-131-50T-STP by Princetel, Inc. of Hamilton, N.J. The fiber optic rotary joint 522 can be made of any suitable material (e.g., stainless steel).

Figure 12:
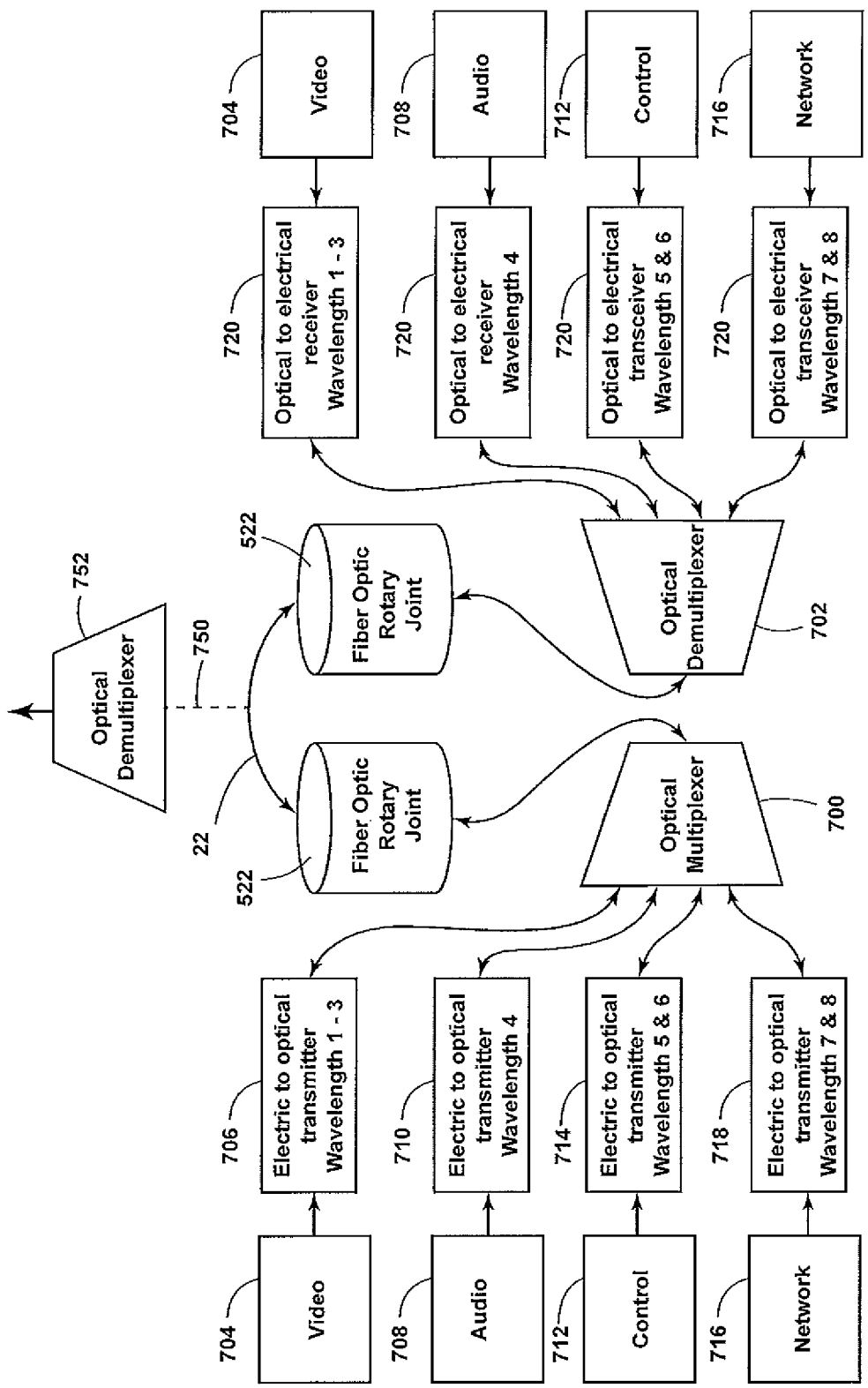
FIG. 12 a schematic view of the data communications across a fiber optic rotary joint using a multiplexer according to the present invention.

In the illustrated embodiment, the data passing through the fiber optic cable 500 can be subjected to an optical multiplexer 700 before the data passes through the fiber optic rotary joint 522 and then passed through an optical demultiplexer 702 before passing the data to the wired medical unit 16. For example, as illustrated in FIG. 12, a plurality of video signals 704 can be passed through an electric to optical transceiver 706, with each of the video signals 704 having different wavelengths, before the video signals 704 are passed to the optical multiplexer 700. Furthermore, an audio signal 708 can be passed through an electric to optical transceiver 710 before the audio signal 708 is passed to the optical multiplexer 700. Moreover, a plurality of control signals 712 can be passed through an electric to optical transceiver 714, with each of the control signals 712 having different wavelengths, before the control signals 712 are passed to the optical multiplexer 700. Likewise, a plurality of network signals 716 can be passed through an electric to optical transceiver 718, with each of the network signals 716 having different wavelengths, before the network signals are passed to the optical multiplexer 700. Each of the video signals 704, the audio signal 708, the control signals 712 and the network signals 716 are at different wavelengths before the signals are passed to the optical multiplexer 700, where the signals are combined. The optical demultiplexer 702 separates the signals and optical to electrical transceivers 720 will transform the video signals 704, the audio signal 708, the control signals 712 and the network signals 716 from optical signals to electrical signals. The optical multiplexer 700 and the optical demultiplexer 702 allow for multiple signals to be passed through the fiber optic cable 500 and the fiber optic rotary joints 522. Use of the optical multiplexer 700 and the optical demultiplexer 702 for passing multiple signals through cables is well known to those skilled in the art. Using the optical multiplexer 700 and the optical demultiplexer 702, multiple data can be sent through a single wire. For example, an HDMI signal with 4 k resolution along with a bidirectional Ethernet signal through the fiber optic cable 500. Although the optical multiplexer 700 is referred to as a multiplexer and the optical demultiplexer 702 is referred to as a demultiplexer, both the optical multiplexer 700 and the optical demultiplexer 702 are both multiplexers and demultiplexers because the data flows in both directions (i.e., is bidirectional). It is contemplated that circulators could be used in concert with the optical multiplexer 700 and the optical demultiplexer 702 to double the capacity of the fiber optic cable 500.

The suspension arm assembly 10 of the present invention is illustrated as having the arms 12 in a single line having a single end point such that only two arms 12 meet at the infinite rotation joints. However, it is contemplated that three or more arms 12 could meet at a single joint. In such an arrangement, at least one of the ground wires 502, the AC power wires 504, the low voltage wires 506, the twisted pairs of serial data wires 508, the coaxial cables 510 and the fiber optic cable 500 could continue along each branch of the arms 12 at the infinite rotation joints. Furthermore, it is contemplated that the wires and/or cables could be split at the infinite rotation joints such that the power and data is sent along each branch of arms 12 to the wire medical units 16 at the end of each branch. FIG. 12 illustrates a situation wherein the data from the optical multiplexer 700 is split off into a branch line 750 at an infinite rotation joint and sent to a second optical demultiplexer 752 before being sent to an optical to electrical transceivers 720 and ultimately to a second wired medical unit 16.

In an aspect of the present invention, multiple data and power signals can be sent along the arms 12 of the suspension arm assembly 10 having multiple infinite rotation joints with unlimited range (i.e., unlimited range of rotation and number of rotations). Therefore, the suspension arm assembly 10 allows for a large data transfer rate while simultaneously allowing the suspension arm assembly 10 to be fully and easily adjustable to any desired location. The arms 12 can be made of any material (e.g., plastic and/or metal) and can be sealed to prevent contamination from entering the suspension arm assembly 10, Furthermore, the arms 12 can have any cross-sectional shape (e.g., square, circular and/or rectangular). Moreover, it is contemplated that the suspension arm assembly 10 could include mechanisms to hold the arms 12 in a particular rotated position (e.g., springs, balls, wedges, toggles, etc.). Additionally, it is contemplated that the cabling 22 could have one or a plurality of connectors (e.g., a SC, LC, FC, ST, SMA or pigtail type connector) within each arm for connecting a first part of the cabling in an arm to a second part of the cabling in an arm (e.g., to assist in routing the cabling 22 through each arm). Furthermore, it is contemplated that the cabling 22 only need to extend to an end item requiring the high definition data to be sent thereto (e.g., if a monitor is directly connected the extension arm 26, the fiber optic cable could only travel through the first infinite rotation joint 28 to the monitor, with other cabling traveling through the arms 12 to another area of the arms). If the cabling 22 does not travel to the end of the arms 12, it is contemplated that the arms after the end of the cabling do not need to have any further infinite rotation joints. Furthermore, it is contemplated that less than all of the joints of the suspension arm assembly 10 could have infinite rotation. For example, it is contemplated that the first joint 28 or both the first joint 28 and the second joint 30 could include stops preventing unlimited rotation at these joints. In such a situation, it is contemplated that the infinite rotation fiber optic and slip ring joint 14 could still be used at these joints to transmit power and data, only with stops limiting rotation, or that these joints could have other configurations for transmitting power and data with mechanical stops limiting rotation (with, for example, all of the wiring passing directly through these joints).

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A medical suspension arm assembly comprising:

a plurality of suspension arms, each adjacent pair of the suspension arms being connected to each other by a joint, with at least one of the joints comprising an infinite rotation joint;

the infinite rotation joint allowing the suspension arms at the infinite rotation joint to have unlimited rotation relative to one another, the infinite rotation joint comprising an electrical contact assembly and an infinite rotation fiber optic joint mounted within the electrical contact assembly, wherein the electrical contact assembly comprises a first portion that comprises a plurality of first electrical contacts and a second portion that comprises a plurality of second electrical contacts that contact the plurality of first electrical contacts, wherein the first portion is rotatably mounted to the second portion such that the plurality of first electrical contacts can rotate relative to the plurality of second electrical contacts, wherein the infinite rotation fiber optic joint comprises a rotor portion that is directly rotatably connected to a stator portion of the infinite rotation fiber optic joint, wherein the rotor portion is mounted to the first portion of the electrical contact assembly and the stator portion is mounted to the second portion of the electrical contact assembly, wherein a first end of the infinite rotation fiber optic joint is infinitely rotatable relative to a second end of the infinite rotation fiber optic joint about an axis that extends centrally through both the first end and the second end;

cabling including fiber optic cabling and at least one electrical power supply wire extending through each of the suspension arms and each joint, wherein a first fiber optic cable is connected centrally to the first end of the infinite rotation fiber optic joint and a second fiber optic cable is connected centrally to the second end of the infinite rotation fiber optic joint, and wherein the first fiber optic cable and the second fiber optic cable directly interface each other through the infinite rotation fiber optic joint; and a wired medical unit connected to an end of the plurality of suspension arms;

wherein data and electrical power can be transferred along each one of the suspension arms through the cabling and across each joint, and wherein at least a portion of the data can be transferred through the infinite rotation fiber optic joint.

2. The medical suspension arm assembly of claim 1, wherein:

the plurality of suspension arms includes two suspension arms.

3. The medical suspension arm assembly of claim 1, wherein:

the data comprises video that can be transmitted through each of the suspension arms and through each infinite rotation joint as light in at least one selected wavelength.

4. The medical suspension arm assembly of claim 1, wherein:

the at least one electrical power supply wire comprises an AC power wire.

5. The medical suspension arm assembly of claim 4, wherein:

the cabling further includes at least one of the following: a ground wire, a low voltage wire, a twisted pair of serial data wires and a coaxial cable.

6. The medical suspension arm assembly of claim 1, wherein:

the cabling leads into and out of the electrical contact assembly, and the electrical power passes through at least a portion of the first and second electrical contacts.

7. The medical suspension arm assembly of claim 6, wherein:

the first portion is a slip ring stator portion and the second portion is a slip ring rotor portion, and the slip ring stator portion has unlimited rotation relative to the slip ring rotor portion, with the power passing between the slip ring stator portion and the slip ring rotor portion to pass the power through the infinite rotation slip ring assembly.

8. The medical suspension arm assembly of claim 7, wherein:

the stator portion of the infinite rotation fiber optic joint has unlimited rotation relative to the rotor portion of the infinite rotation fiber optic joint, with the at least a portion of the data passing between the stator portion and the rotor portion to pass the at least a portion of the data through the infinite rotation fiber optic joint.

9. The medical suspension arm assembly of claim 8, wherein:

the cabling further includes at least one further wiring element comprising a ground wire, a low voltage wire, a twisted pair of serial data wires or a coaxial cable; and the electrical contact assembly connects a first portion of the at least one further wiring element to a second portion of the at least one further wiring element.

10. The medical suspension arm assembly of claim 1, further including:

at least one multiplexer for multiplexing the at least a portion of the data traveling through the cabling.

11. The medical suspension arm assembly of claim 1, wherein:

the wired medical unit is a video monitor.

12. The medical suspension arm assembly of claim 1, further including:

a ceiling attachment member connected to the plurality of suspension arms by a ceiling infinite rotation joint for connecting the plurality of suspension arms to a ceiling, the ceiling infinite rotation joint allowing the plurality of suspension arms to have unlimited rotation relative to the ceiling attachment member, the data and the electrical power being transferred to the plurality of suspension arms through the ceiling attachment member and the ceiling infinite rotation joint.

13. The medical suspension arm assembly of claim 1, wherein:

at least two adjacent pairs of the suspension arms are connected by the infinite rotation joint.

14. The medical suspension arm assembly of claim 1, wherein the at least a portion of the data that can be transferred through the infinite rotation fiber optic joint comprises high definition video.

15. A medical suspension arm assembly comprising:

a ceiling attachment member for connecting the medical suspension arm assembly to a ceiling;

a first arm;

a first rotational joint rotationally connecting the ceiling attachment member to the first arm;

at least one second arm;

a second rotational joint rotationally connecting the first arm to the at least one second arm;

a wired medical support;

a third rotation joint rotationally connecting the at least one second arm to the wired medical support; and data lines including at least one fiber optic cable extending through the ceiling attachment member, the first rotational joint, the first arm, the second rotational joint, the at least one second arm and the third rotational joint to the wired medical unit support;

wherein data can be transferred along the data lines from the ceiling attachment member to the wired medical unit support; and wherein at least one of the first rotational joint, the second rotational joint and the third rotational joint is an infinite rotation joint that allows for infinite rotation, the infinite rotation joint comprising an electrical contact assembly and an infinite rotation fiber optic joint mounted within the electrical contact assembly, wherein the electrical contact assembly comprises a first portion that comprises a plurality of first electrical contacts and a second portion that comprises a plurality of second electrical contacts that contact the plurality of first electrical contacts, wherein the first portion is rotatably mounted to the second portion such that the plurality of first electrical contacts can rotate relative to the plurality of second electrical contacts, wherein the infinite rotation fiber optic joint comprises a rotor portion that is directly rotatably connected to a stator portion of the infinite rotation fiber optic joint, wherein the rotor portion is mounted to the first portion of the electrical contact assembly and the stator portion is mounted to the second portion of the electrical contact assembly, wherein a first end of the infinite rotation fiber optic joint is infinitely rotatable relative to a second end of the infinite rotation fiber optic joint about an axis that extends centrally through both the first end and the second end, and wherein a first fiber optic cable is connected centrally to the first end of the infinite rotation fiber optic joint and a second fiber optic cable is connected centrally to the second end of the infinite rotation fiber optic joint, the first fiber optic cable and the second fiber optic cable directly interface each other through the infinite rotation fiber optic joint, and at least a portion of the data can be transferred through the infinite rotation fiber optic joint.

16. The medical suspension arm assembly of claim 15, wherein:

the at least one second arm comprises a single second arm.

17. The medical suspension arm assembly of claim 15, wherein:
the data comprises video that can be transmitted through each of the arms and through each of the infinite rotation joints as light in at least one selected wavelength.

18. The medical suspension arm assembly of claim 17, further including:
power lines extending through the ceiling attachment member, the first infinite rotation joint, the first arm, the second infinite rotation joint, the at least one second arm and the third infinite rotation joint to the wired medical unit support;
wherein the power lines can transmit AC power.

19. The medical suspension arm assembly of claim 18, further including:
at least one further wiring element comprising at least one of the following: a ground wire, a low voltage wire, a twisted pair of serial data wires and a coaxial cable;
wherein the further wiring element extends through the ceiling attachment member, the first infinite rotation joint, the first arm, the second infinite rotation joint, the at least one second arm and the third infinite rotation joint to the wired medical unit.

20. The medical suspension arm assembly of claim 18, wherein:
the data lines lead into and out of the electrical contact assembly, and the power passes through at least a portion of the first and second electrical contacts.

21. The medical suspension arm assembly of claim 20, wherein:
the first portion is a slip ring stator portion and the second portion is a slip ring rotor portion, and the slip ring stator portion has unlimited rotation relative to the slip ring rotor portion, with the power passing between the slip ring stator portion and the slip ring rotor portion to pass the power through the slip ring assembly.

22. The medical suspension arm assembly of claim 21, wherein:
the stator portion of the infinite rotation fiber optic joint has unlimited rotation relative to the rotor portion of the infinite rotation fiber optic joint, with the at least a portion of the data passing between the stator portion and the rotor portion to pass the at least a portion of the data through the infinite rotation fiber optic joint.

23. The medical suspension arm assembly of claim 21, further including:
at least one further wiring element comprising a ground wire, a low voltage wire, a twisted pair of serial data wires or a coaxial cable; and
wherein the electrical contact assembly connects a first portion of the at least one further wiring element to a second portion of the at least one further wiring element.

24. The medical suspension arm assembly of claim 15, further including:
at least one multiplexer for multiplexing the at least a portion of the data traveling through the data lines.

25. The medical suspension arm assembly of claim 15, wherein:
the second rotational joint and the third rotational joint are infinite rotation joints that allow for unlimited rotation of the first arm relative to the second arm and unlimited rotation of the at least one second arm relative to the wired medical support.

26. The medical suspension arm assembly of claim 15, wherein the at least a portion of the data that can be transferred through the infinite rotation fiber optic joint comprises high definition video.

27. A medical suspension arm assembly comprising:
a plurality of suspension arms, each adjacent pair of the suspension arms being connected to each other by a joint, with at least one of the joints comprising an infinite rotation joint;
the infinite rotation joint allowing the suspension arms at the infinite rotation joint to have unlimited rotation relative to one another, the infinite rotation joint comprising an electrical contact assembly and an infinite rotation fiber optic joint mounted within the electrical contact assembly, wherein the electrical contact assembly comprises a first portion that comprises a plurality of first electrical contacts and a second portion that comprises a plurality of second electrical contacts that contact the plurality of first electrical contacts, wherein the first portion is rotatably mounted to the second portion such that the plurality of first electrical contacts can rotate relative to the plurality of second electrical contacts, wherein the infinite rotation fiber optic joint comprises a rotor portion that is directly rotatably connected to a stator portion of the infinite rotation fiber optic joint, wherein the rotor portion is mounted to the first portion of the electrical contact assembly and the stator portion is mounted to the second portion of the electrical contact assembly, wherein a first end of the infinite rotation fiber optic joint is infinitely rotatable relative to a second end of the infinite rotation fiber optic joint about an axis that extends centrally through both the first end and the second end;
a wired medical unit support connected to the plurality of suspension arms; and
cabling including fiber optic cabling and at least one electrical power supply wire extending through at least one of the suspension arms and each joint to the wired medical unit support, wherein a first fiber optic cable is connected to the first end of the infinite rotation fiber optic joint and a second fiber optic cable is connected centrally to the second end of the infinite rotation fiber optic joint, and wherein the first fiber optic cable and the second fiber optic cable directly interface each other through the infinite rotation fiber optic joint;
wherein data and electrical power can be transferred along the at least one of the suspension arms through the cabling and across the at least one infinite rotation joint to the wired medical unit support, and wherein at least a portion of the data can be transferred through the infinite rotation fiber optic joint.

28. The medical suspension arm assembly of claim 27, wherein:
the plurality of suspension arms includes two suspension arms.

29. The medical suspension arm assembly of claim 27, wherein:
the data comprises video that can be transmitted through each of the suspension arms and through each infinite rotation joint as light in at least one selected wavelength.

30. The medical suspension arm assembly of claim 29, wherein:
the at least one electrical power supply wire comprises an AC power wire.

31. The medical suspension arm assembly of claim 30, wherein:
the cabling further includes at least one of the following: a ground wire, a low voltage wire, a twisted pair of serial data wires and a coaxial cable.

32. The medical suspension arm assembly of claim 27, wherein:
the cabling leads into and out of the electrical contact assembly, and the electrical power passes through at least a portion of the first and second electrical contacts.

33. The medical suspension arm assembly of claim 32, wherein:
the first portion is a slip ring stator portion and the second portion is a slip ring rotor portion, and the slip ring stator portion has unlimited rotation relative to the slip ring rotor portion, with the power passing between the slip ring stator portion and the slip ring rotor portion to pass the power through the infinite rotation slip ring assembly.

34. The medical suspension arm assembly of claim 33, wherein:
the stator portion of the infinite rotation fiber optic joint has unlimited rotation relative to the rotor portion of the infinite rotation fiber optic joint, with the at least a portion of the data passing between the stator portion and the rotor portion to pass the at least a portion of the data through the infinite rotation fiber optic joint.

35. The medical suspension arm assembly of claim 34, wherein:
the cabling further includes at least one further wiring element comprising a ground wire, a low voltage wire, a twisted pair of serial data wires or a coaxial cable; and
the electrical contact assembly connects a first portion of the at least one further wiring element to a second portion of the at least one further wiring element.

36. The medical suspension arm assembly of claim 27, further including:
at least one multiplexer for multiplexing the at least a portion of the data traveling through the cabling.

37. The medical suspension arm assembly of claim 27, further including:
a ceiling attachment member connected to the plurality of suspension arms by a ceiling infinite rotation joint for connecting the plurality of suspension arms to a ceiling, the ceiling infinite rotation joint allowing the plurality of suspension arms to have unlimited rotation relative to the ceiling attachment member, the data and the electrical power being transferred to the plurality of suspension arms through the ceiling attachment member and the ceiling infinite rotation joint.

38. The medical suspension arm assembly of claim 27, wherein:
at least two adjacent pairs of the suspension arms are connected by the infinite rotation joint.

39. The medical suspension arm assembly of claim 27, wherein the at least a portion of the data that can be transferred through the infinite rotation fiber optic joint comprises high definition video.

* * * * *